United States Patent [19]

Itabashi et al.

[11] Patent Number: 5,714,757
[45] Date of Patent: Feb. 3, 1998

[54] SURFACE ANALYZING METHOD AND ITS APPARATUS

[75] Inventors: Naoshi Itabashi, Hachioji; Kozo Mochiji, Tokorozawa; Hiroyasu Shichi, Tanashi; Seiji Yamamoto, Hachioji; Satoshi Osabe, Kokubunji; Keiichi Kanehori, Sayama, all of Japan

[73] Assignee: Hitachi, Ltd., Tokyo, Japan

[21] Appl. No.: 542,562

[22] Filed: Oct. 13, 1995

[30] Foreign Application Priority Data

Oct. 14, 1994 [JP] Japan .................. 6-249070

[51] Int. Cl.⁶ .................................................. H01J 37/08
[52] U.S. Cl. .......................... 250/309; 250/305; 250/307
[58] Field of Search ............................ 250/309, 305, 250/396 R, 492.2, 307

[56] References Cited

U.S. PATENT DOCUMENTS 5,327,475   7/1994   Golovanivsky et al. ............ 378/34

OTHER PUBLICATIONS

E. S. Parilis et al; "Atomic Collisions on Solid Surface", North–Holland Publisher, 1992, chap. 12 (Cited on p. 2, line 17–18 in our specification).

P. Varga et al.; Nucl. Instrum. & Meth. B58 (1990) 417. (Cited on p. 2, line 20–21 in our specification).

U. Diebold and P. Varga; "Desorption Induced by Electronic Transitions IV", Springer–Verlag, 1990, p. 193. (Cited on p. 2, line 21–23 in our specification).

*Primary Examiner*—Bruce Anderson
*Attorney, Agent, or Firm*—Antonelli, Terry, Stout & Kraus, LLP

[57] ABSTRACT

A surface analyzing method comprising an ion generation step for generating multiply-charged ions of specific ion species and specific charge state; a deceleration step for decelerating the generated multiply-charged ions to a lower kinetic energy than an energy of threshold of sputtering of an objective material; an irradiation step for irradiating the decelerated multiply-charged ions on the surface of a sample; and an analysis step for analyzing particles or light emitted from the surface of said sample by the irradiation of said multiply-charged ions. Apparatus is provided for carrying out the method. Since the ions irradiated on the sample surface are multiply-charged ions having a lower kinetic energy than that of threshold of sputtering of materials constituting a sample, the irradiated ions interact merely with the top surface layer of the sample whereby analyzed information merely from the top surface layer of the sample can be obtained, and as a result, the kind of atoms of the top surface layer of the sample and the bonding state of said atoms can be analyzed with high sensitivity and high resolution.

32 Claims, 12 Drawing Sheets

FIG. 14

| ITEMS / METHODS | | THIS INVENTION | | PREVIOUS SIMS, PREVIOUS SNMS | PREVIOUS e-AES X-AES | PREVIOUS XPS | PREVIOUS UPS | PREVIOUS INS | PREVIOUS MDS |
|---|---|---|---|---|---|---|---|---|---|
| | | MCI-SIMS MCI-SNMS | MCI-AES | | | | | | |
| PRINCIPLE OF MEASUREMENT | PROBE | MCI (Ek<Eth) | MCI (Ek<Eth) | SCI (Ek>Eth) | ELECTRON, PHOTON (A FEW HUNDREDS-A FEW THOUSANDS OF eV) | PHOTON (A FEW HUNDREDS-A FEW THOUSANDS OF eV) | PHOTON (A FEW-A FEW TENS OF eV) | SCI (Ek<Eth) | METASTABLE ATOM (Ek<Eth) |
| | DETECTION | SECONDARY ION SECONDARY NEUTRAL (POTENTIAL EMISSION) | AUGER ELECTRON (CORE LEVEL) | SECONDARY ION (KINETIC EMISSION) | AUGER ELECTRON (CORE LEVEL) | PHOTO-ELECTRON (CORE LEVEL) | PHOTO-ELECTRON (VALENCE BAND) | AUGER ELECTRON (VALENCE BAND) | AUGER ELECTRON (VALENCE BAND) |
| | PHYSICS | COULOMB INTERACTION | HOLE FORMATION (CORE LEVEL), AUGER ELECTRON EMISSION | KINETIC SPUTTERING | HOLE FORMATION (CORE LEVEL), AUGER ELECTRON EMISSION | PHOTO-ELECTRON EMISSION (FROM CORE LEVEL) | PHOTO-ELECTRON EMISSION (FROM VALENCE BAND) | HOLE FORMATION (VALENCE BAND), AUGER ELECTRON EMISSION | HOLE FORMATION (VALENCE BAND), AUGER ELECTRON EMISSION |
| INFORMATION | | KIND OF ELEMENT, BONDING STATE (HIGH RELIABILITY) | KIND OF ELEMENT, BONDING STATE (HIGH RELIABILITY) | KIND OF ELEMENT (HIGH RELIABILITY) | KIND OF ELEMENT, BONDING STATE (HIGH RELIABILITY) | KIND OF ELEMENT, BONDING STATE (HIGH RELIABILITY) | KIND OF ELEMENT, BONDING STATE (PRESUMPTION) | KIND OF ELEMENT, BONDING STATE (PRESUMPTION) | KIND OF ELEMENT, BONDING STATE (PRESUMPTION) |
| FEATURE | | SENSITIVITY FOR TOP SURFACE LAYER, HIGH SENSITIVITY | SENSITIVITY FOR TOP SURFACE LAYER, HIGH SENSITIVITY | SENSITIVITY FOR SEVERAL LAYERS FROM THE SURFACE DISTURBANCE OF ATOMIC CONFIGURATION | SENSITIVITY FOR SEVERAL LAYERS FROM THE SURFACE | SENSITIVITY FOR SEVERAL LAYERS FROM THE SURFACE | SENSITIVITY FOR SEVERAL LAYERS FROM THE SURFACE | SENSITIVITY FOR TOP SURFACE LAYER | SENSITIVITY FOR TOP SURFACE LAYER |
| REMARKS | | NO INFLUENCE BY KINETIC SPUTTERING | HOLE FORMATION IN VERY SHALLOW REGION OF THE MATERIAL | DAMAGE CAUSED BY KINETIC SPUTTERING | HOLE FORMATION IN THE INTERNAL PART OF THE MATERIAL (SURVIVAL OF DAMAGE IN THE MATERIAL) | | | NECESSARY FOR PRELIMINARY PRESUMPTION ABOUT KIND OF ELEMENT AND BONDING STATE | |

NOTES)
MCI ··· MULTIPLY-CHARGED ION
SIMS ··· SECONDARY ION MASS SPECTROMETRY
AES ··· AUGER ELECTRON SPECTROSCOPY
MDS ··· METASTABLE-ATOM DE-EXCITATION SPECTROSCOPY
INS ··· ION NEUTRALIZATION SPECTROSCOPY
Ek ··· KINETIC ENERGY
Eth ··· THRESHOLD OF KINETIC SPUTTERING
SCI ··· SINGLY-CHARGED ION
SNMS ··· SPUTTERED NEUTRAL MASS SPECTROMETRY
XPS ··· X-RAY PHOTO-ELECTRON SPECTROSCOPY
UPS ··· ULTRA-VIOLET PHOTO-ELECTRON SPECTROSCOPY

SURFACE ANALYZING METHOD AND ITS APPARATUS

BACKGROUND OF THE INVENTION

The present invention relates to a method and apparatus for analyzing a surface condition of materials used in various fields, and more particularly to a method and apparatus for analyzing a kind of particles present on a top layer of a material surface and a bonding state thereof.

In the past, as methods for carrying out an analysis of a composition of elements of a specimen surface and a bonding state thereof, mainly the following two methods have been used.

A first method includes an Auger electron spectroscopy, a photo-electron spectroscopy, a secondary ion mass spectrometry, a sputtered neutral mass spectrometry and the like, which methods comprise irradiating an electron beam, light, an accelerated ion beam and the like on a specimen surface, and detecting an electron, an ion and the like emitted from the specimen surface to carry out the analysis of the specimen surface.

A second method includes a metastable atom deexcited electron spectroscopy, an ion neutralization spectroscopy and the like, which methods comprise irradiating an excited atom (such as a metastable He atom) and an ion (such as He ion), and measuring an electron emitted from top surface layer to analyze the bonding state of atoms on the top surface layer.

Recently, the study on the interaction between a multiply-charged ion and a solid surface has been started. Up to now, there are a report example in which when a multiply-charged ion having a large kinetic energy than a threshold of sputtering of an objective material is irradiated on a surface of a solid specimen, electrons are emitted from the specimen surface (for example, E. S. Parilis et al; "Atomic Collisions on Solid Surface", North-Holland Publisher, 1992, chap. 12) and a report example in which ions and neutrals are emitted (for example, P. Varga et al.; Nucl. Instrum. & Meth. B58 (1990) 417 and U. Diebold and P. Varga; "Desorption Induced by Electronic Transitions IV", Springer-Verlag, 1990, p. 193).

Among the above-described reports, P. Varga et al. mention their comments in that "In order that a multiply-charged ion electronically interacts with a solid surface to emit particles constituting the solid surface, the effect of kinetic energy is not at all unnecessary but it is necessary to impart some kinetic energy to the multiply-charged ion". In the above described report example, the reason why the multiply-charged ion have a larger kinetic energy than a threshold of sputtering of a solid specimen is considered on the basis of the fact that the effect of the kinetic energy is essential in order that a multiply-charged ion electronically interacts with a surface of a solid specimen.

Recently, with the trend of a finer configuration of a semiconductor element, there has been required a technique in which atomic layers on the semiconductor surface are removed one by one, or reversely, the atomic layers are grown one by one. In order to develop these techniques, it is essential that a composition of elements on the top layer of the semiconductor surface and a bonding state thereof can be evaluated.

However, in the above-described first method, the particles and light irradiated on the specimen enter the inner layer portion of the specimen, and therefore, information obtained is average of a plurality of atomic layers on the specimen surface, failing to obtain information of only the top surface layer (single layer).

Further, in the above-described second method, since a potential energy of an excited atom or a singly-charged ion is small, a core electron on the surface cannot be excited, and only a charged electron or a transmission electron is to be excited. Because of this, a measured electron spectrum has not a peak peculiar to a core electron emitted from the surface and is formed into a featureless shape which is unclear in construction, as a result of which analysis of the spectrum becomes relatively complicated. Accordingly, the kind of atoms and the state of electrons need be predicted in advance to some extent in order to determine the bonding state of atoms on the top surface layer from the results of the measurement. However, in the case that there is a contamination whose true character is unknown on the top surface layer and the kind of atoms constituting the contamination and the bonding state thereof are desired to be clarified, these measuring methods are in fact helpless.

On the other hand, with respect to the interaction between the multiply-charged ion and the surface of the solid specimen, there has been reported a phenomenon in which the multiply-charged ion having a higher kinetic energy than a threshold of sputtering of the solid material is irradiated on the surface of the solid specimen whereby the electrons, ion species and neutral species are emitted from the specimen surface, as previously mentioned. Even if an attempt is made to utilize this phenomenon for surface analysis, the irradiated multiply-charged ion affects the inner layer portion of the specimen surface as long as the multiply-charged ion is irradiated on the solid surface with such a high kinetic energy. This fact is similar to the case in which the above-described first method is used. That is, the information obtained is average of the plural atomic layers on the specimen surface, and information from only the top surface layer (single atomic layer) cannot be obtained.

Among the above-described first methods, in the method of making use of the particle having a larger kinetic energy than a threshold of sputtering of an objective solid or the method of irradiating the multiply-charged ion on the solid specimen having a larger kinetic energy than a threshold of sputtering of an objective material, the destruction of a lattice occurs not only in the top surface layer of the solid specimen to be measured but also in the inner layer of the specimen, and therefore, the damage of the underlying layer caused by the measurement cannot be avoided. Further, in the above-described first method, energy cannot be poured into only the top surface layer concentratively. In the above-described second method, energy can be poured into only the top surface layer but since the energy value itself is small, it is extremely disadvantageous in terms of sensitivity of measurement.

As described above, there has been heretofore considered that in order that the multiply-charged ion electronically interacts with the solid surface, the effect of the kinetic energy is not at all unnecessary but some kinetic energy is necessary. Actually, no report has been-made of the case in which the multiply-charged ion is irradiated on the surface of the solid specimen with the kinetic energy thereof sufficiently lowered than the threshold of sputtering of the objective material. That is, it has been considered to be actually impossible that the kinetic energy of the irradiated multiply-charged ion is set to a value less than the threshold of sputtering of the objective material, which is used for surface analysis.

Recently, the present inventors found that a multiply-charged ion of argon is irradiated on a GaAs specimen with kinetic energy decelerated to a value less than a threshold of sputtering of GaAs and particles emitted from the specimen surface are analyzed, as a result of which even in the case that the multiply-charged ion is irradiated on the surface of the solid specimen with the kinetic energy of the irradiated multiply-charged ion sufficiently lowered than the threshold of sputtering of the objective material, the interaction between the irradiated multiply-charged ion and the surface of the solid specimen is obtained for surface analysis. Thereby, there is obtained a prospect that the multiply-charged ion with kinetic energy decelerated to a value less than the threshold of sputtering of the objective material can be utilized for surface analysis.

SUMMARY OF THE INVENTION

An object of the present invention is to provide a surface analyzing method in which a multiply-charged ion having a kinetic energy less than a threshold of sputtering of an objective material is utilized to overcome problems of the above-described (first and second) prior arts and of a prior art making use of a multiply-charged ion having a larger kinetic energy than a threshold of sputtering of an objective material, whereby a composition of elements of the top surface layer of a solid specimen and a bonding state of these elements can be measured without giving a damage to an underlying layer and with high sensitivity.

For achieving the aforementioned object, according to the present invention, there is provided a surface analyzing method comprising: an ion generation process for generating multiply-charged ions of desired ion species and desired charge state, a deceleration process for decelerating the generated multiply-charged ion to a lower kinetic energy than that of a threshold of sputtering of an objective material, an irradiation process for irradiating the decelerated multiply-charged ion on the surface of a specimen, and an analysis process for analyzing particles or light emitted from the surface of the specimen by the irradiation of the multiply-charged ion.

According to the present invention, there is further provided a surface analyzing apparatus comprising: an ion generator for generating multiply-charged ions of desired ion species and desired charge state, a decelerator for decelerating the generated multiply-charged ion to a lower kinetic energy than that of a threshold of sputtering of an objective material, an irradiator for irradiating the decelerated multiply-charged ion on the surface of a specimen, and an analyzing means for analyzing particles or light emitted from the surface of the specimen by the irradiation of the multiply-charged ion.

The multiply-charged ion termed herein means an ion in a state where two electrons or more are stripped of an atom, the larger the charge state (number of electrons stripped of), electrons at deep energy levels (that is, of an core) are lost. Therefore, the larger the charge state, the energy (ionized energy) required for generation of the multiply-charged ion becomes high (because electrons of the core have to be removed). This also means that the multiply-charged ion having a large charge state has high potential energy corresponding to the high ionized energy. Further, the multiply-charged ion also has kinetic energy along with the above-described potential energy.

As shown in FIGS. 17A and 17B, when a multiply-charged ion 1 approaches the surface of the solid specimen, among electrons of specimen surface atoms 2, an electron at a shallower energy level than an energy level of a hole (state with the electron lost) of the multiply-charged ion 1 tends to be transferred to a hole level of the multiply-charged ion 1. Such transfer of the electron from the surface atoms 2 to the hole of the multiply-charged ion 1 is called an Auger neutralization. Indeed, the electron of the surface atoms 2 at the energy level equal to the hole level of the multiply-charged ion 1 is sometimes transferred to the hole (which is called a resonance neutralization). As the result of the transfer of these charges, the electrons at the shallower energy levels are transferred so as to fill the hole levels formed in the surface atoms 2. At this time, an electron receives kinetic energy corresponding to two energy levels participated in the transfer of electrons and is emitted from the specimen surface (this emitted electron is called an Auger electron). Alternatively, a photon (X-ray) having the same energy is emitted in place of the Auger electron. A value of the kinetic energy of the Auger electron and of the photon energy of X-ray is peculiar to atoms which emit them. This value is measured whereby the kind of atoms present on the specimen can be determined. It is known that the value of the kinetic energy of the Auger electron or the photon energy of X-ray slightly varies with the bonding state even in the same atom. The bonding state of atoms can be determined from the measurement of this variation.

On the other hand, with the transfer of electrons from the surface electrons 2 of the solid specimen to the multiply-charged ion 1 and the emission of the Auger electron, a plurality of holes are formed on the surface layer of the solid specimen. Here, if as the multiply-charged ion 1, a multiply-charged ion having a sufficiently high charge state is used, the emission of particles (atoms) constituting a specimen surface occurs due to a Coulomb repulsive force. This phenomenon can be explained from the fact that the plurality-of ionized surface atoms 2 receive the Coulomb repulsive force generated therebetween to produce a two-dimensional motion in the solid surface, and as a result, one of the plurality of ionized surface atoms 2 is desorbed from the solid surface. Accordingly, it is possible to determine the kind of particles constituting the solid surface by analyzing a mass of a particle (a particle originally present on the solid surface) 3 emitted from the solid surface.

Incidentally, it is reasonable that the particle 3 emitted from the solid surface is an ion of the surface atom 2. However, the results of experiments show that the emission of the neutral-surface atom 2 itself may occur (the cause thereof is unknown). From this fact, it is effective to improve the analysis sensitivity of the solid surface to arrange an auxiliary ionizing means for ionizing the emitted neutral particles in the vicinity of the solid surface on which the multiply-charged ion 1 is irradiated. Further, since the emitted particle 3 from the solid-surface is emitted by the electric repulsive force, it has an initial kinetic energy immediately after the emission (this is also true for the case where it is radiated as a neutral particle). The value of the initial kinetic energy has a property that it varies with the bonding state of particles constituting the solid surface. Accordingly, it is possible to determine the bonding state of particles constituting the solid surface by analyzing the value of the initial kinetic energy.

The above-described matter is common to the emission phenomenon of particle constituting the X-ray, the Auger electron or the specimen surface. In the present invention, the effect obtained by utilization of the multiply-charged ion is that in the case of irradiation of light or electron beams, the irradiated light or electrons enter deep portion of the solid specimen. Whereas, in the case of irradiation of the multiply-charged ion, if the irradiation is made with the kinetic energy set to be smaller than the physical threshold of sputtering of materials constituting the solid specimen, since the size of the multiply-charged ion is large, the irradiated multiply-charged ion cannot enter the inner layer portion of the solid specimen. Thus, the interaction merely with the top surface layer of the solid specimen can occur. While the threshold of the physical sputtering varies with materials constituting a specimen, it has approximately a value in excess of 20 eV. Accordingly, if the multiply-charged ion is irradiated on the specimen surface with the kinetic energy adjusted to a value not more 20 eV, the influence of the physical sputtering can be actually ignored. As described, in the case that the multiply-charged ion is irradiated on the specimen surface after decelerating to a sufficiently small value of the kinetic energy, the Auger electron or X-ray is emitted from only the top surface layer of the specimen, and therefore, information only from the top surface layer can be obtained.

On the other hand, with respect to the emission of the particles themselves constituting the surface of the solid specimen caused by the multiply-charged ion, the point that the emission of the particles constituting the surfaces occurs merely from the top surface layer is similar to the case of the irradiation of the light or electron beams. However, in the case that the multiply-charged ion is irradiated with deceleration, hole formation occurs concentratively in the vicinity of the top surface layer. Therefore, the emission probability of the particles from the top surface layer is extremely high as compared with the case where the light or electron beams are irradiated, as a consequence of which the measuring sensitivity is materially improved.

It is also possible to emit the particles constituting the specimen surface by using a primary ion beam having a higher kinetic energy than a threshold of sputtering of materials constituting a surface of a solid specimen. Actually, this phenomenon is used in a conventional secondary ion mass analyzing method and a sputtering neutral particle mass analyzing method using a primary ion having an extremely larger kinetic energy (scores of 100 eV to scores of 10 keV) than a dynamic threshold of sputtering. However, the emission of particles from the specimen surface caused by the irradiation of ions having such a high kinetic energy exclusively results from the dynamic sputtering, and is totally different in property from the emission of particles due to the electronic interaction in the case that the multiply-charged ion is irradiated with sufficiently small kinetic energy. First, since the dynamic-sputtering influences on the inner layer portion of the solid, it is difficult to obtain information of only the top surface layer by utilization of a primary ion having so large kinetic energy as not to ignore the aforementioned influence. At this time, since the destruction of a lattice extends not only to the top surface layer to be measured but also to the interior of the solid, a damage to the underlying material caused by measurement cannot be avoided. Further, since the energy cannot be merely poured concentratively into the top surface layer, an improvement in the measuring sensitivity cannot be expected. As described, it is essential to decelerate the irradiated ion so that the kinetic energy of the irradiated ion is smaller than the threshold of sputtering of the objective material in order to eliminate the influence of the dynamic sputtering, in order that the interaction is produced limitedly only in the top surface layer. Even if the ion having a kinetic energy not less than the threshold of sputtering without taking this into consideration, it is difficult to obtain information of only the top surface layer without damaging the underlying layer and with high sensitivity. Further, in the conventional secondary ion mass analyzing method or sputtering neutral particle mass analyzing method, a single-charged ion is normally used as a primary ion, but even if a multiply-charged ion is used in place of the single-charged ion, these problems cannot be overcome as long as this multiply-charged ion is irradiated on the solid surface with high kinetic energy as in prior art.

However, if the multiply-charged ion is irradiated on the specimen surface after the kinetic energy is adjusted to be smaller than the threshold of sputtering of the objective material, all the problems including the depth resolution at levels posing the problem of the top surface layer, the damage of the underlying layer and the measuring sensitivity are solved. The comparison of the conventional measuring technique to the measuring technique according to the present invention is summarized and shown in FIG. 14. In FIG. 14, MCI- designates a multiply-charged ion excited; e-, an electron beam excited; and X-, an X-ray excited. Further, SIMS designates a secondary ion mass spectrometry; SNMS, a sputtered neutral mass spectrometry; NMS, a neutral particle mass spectrometry; AES, an Auger electron spectroscopy; XPS, an X-ray photo-electron spectroscopy; UPS, an ultra-violet photo-electron spectroscopy; INS, an ion neutralization spectroscopy; and MDS, a metastable de-excited electron spectroscopy.

As described above, by sufficiently decelerating the multiply-charged ion taking the influence of the dynamic sputtering of the solid material into consideration to utilize it, the composition of elements of the surface and the bonding state can be analyzed by the extreme depth resolution, say, only the top surface layer, and can be measured very advantageously in many aspects such as an improvement in sensitivity and an reduction in damage. Further, as an application of the present method for measurement, if measurement is continuously carried out while sequentially removing particles constituting the surface from the top surface layer using a multiply-charged ion having an extremely high density, it is also possible to analyze the depth distribution of elements with the resolution at levels of the atomic layer. Here, the utilization of the multiply-charged ion beam having a high density is useful for improvement in etching of specimen widthwise and in measuring sensitivity. However, when the density is made excessively high, the influence due to the thermal reaction is expected to appear. However, since the influence due to the thermal reaction can be removed, this problem can be avoided.

The operation of the present invention has been described of the case that the kinetic energy of the irradiated multiply-charged ion is set to a lower value (less than 20 eV) than the threshold of sputtering of the objective material. In the case that the kinetic energy Ek of the irradiated multiply-charged ion is set to a range of 20 eV<Ek≦1 keV, the influence of the dynamic sputtering cannot be avoided. Even in this case, however, many of particles emitted from the specimen surface by the dynamic sputtering are emitted from the top surface layer, and less particles are emitted from the second layer and thereafter. Therefore, when the kinetic energy of the irradiated multiply-charged ion is in the range exceeding 20 eV and not more than 1 keV, the emission of particles due to both the electronic interaction between the multiply-charged ion and the solid surface and the dynamic sputtering action occurs as previously mentioned, but the amount of emission is governed by those from the top surface layer. Accordingly, if the kinetic energy of the irradiated multiply-charged ion is in the range exceeding 20 eV and not more than 1 keV, it is possible to barely measure the top surface layer if a lowering of quality of measuring caused by the disturbance of the lattice of the top surface layer is taken into account. The present inventors insisted that surface measurement of the solid specimen can be made using the multiply-charged ion having a lower kinetic energy than the threshold of sputtering of the objective material, and that the kinetic energy of the multiply-charged ion to be used can be spread to 1 keV if the lowering of quality of measurement to some extent is taken into account. Accordingly, this is different in the gist from an example of conventional study in which a multiply-charged ion having a kinetic energy not less than a threshold of sputtering of an objective solid is used in order to initiate the interaction between the multiply-charged ion and the solid surface on the assumption that the effect of the kinetic energy is essential, as described in the description of prior art. In the case that the kinetic energy of the irradiated multiply-charged ion is a value exceeding 1 keV, the emission of particles from the top surface layer is not influential any longer, and the influence of the damage (destruction of lattice) on the second layer and thereafter cannot be ignored. Accordingly, the features of the present invention are materially impaired such that under the condition that the kinetic energy of the irradiated multiply-charged ion exceeds 1 keV, the electronic interaction between the irradiated multiply-charged ion and the solid surface can be utilized to measure the top surface layer of the solid and the damage given to the underlying layer can be reduced.

These and other objects and many of the attendant advantages of the invention will be readily appreciated as the same becomes better understood by reference to the following detailed description when considered in connection with the accompanying drawings.

BRIEF DESCRIPTION OF THE DRAWINGS

FIG. 14 is a table showing comparison between a surface measurement technique according to the present invention and a conventional known measurement technique;

DETAILED DESCRIPTION OF THE PREFERRED EMBODIMENTS

Embodiments of the present invention will be described hereinafter in detail with reference to the drawings.

<Embodiment 1>

Figure 1:
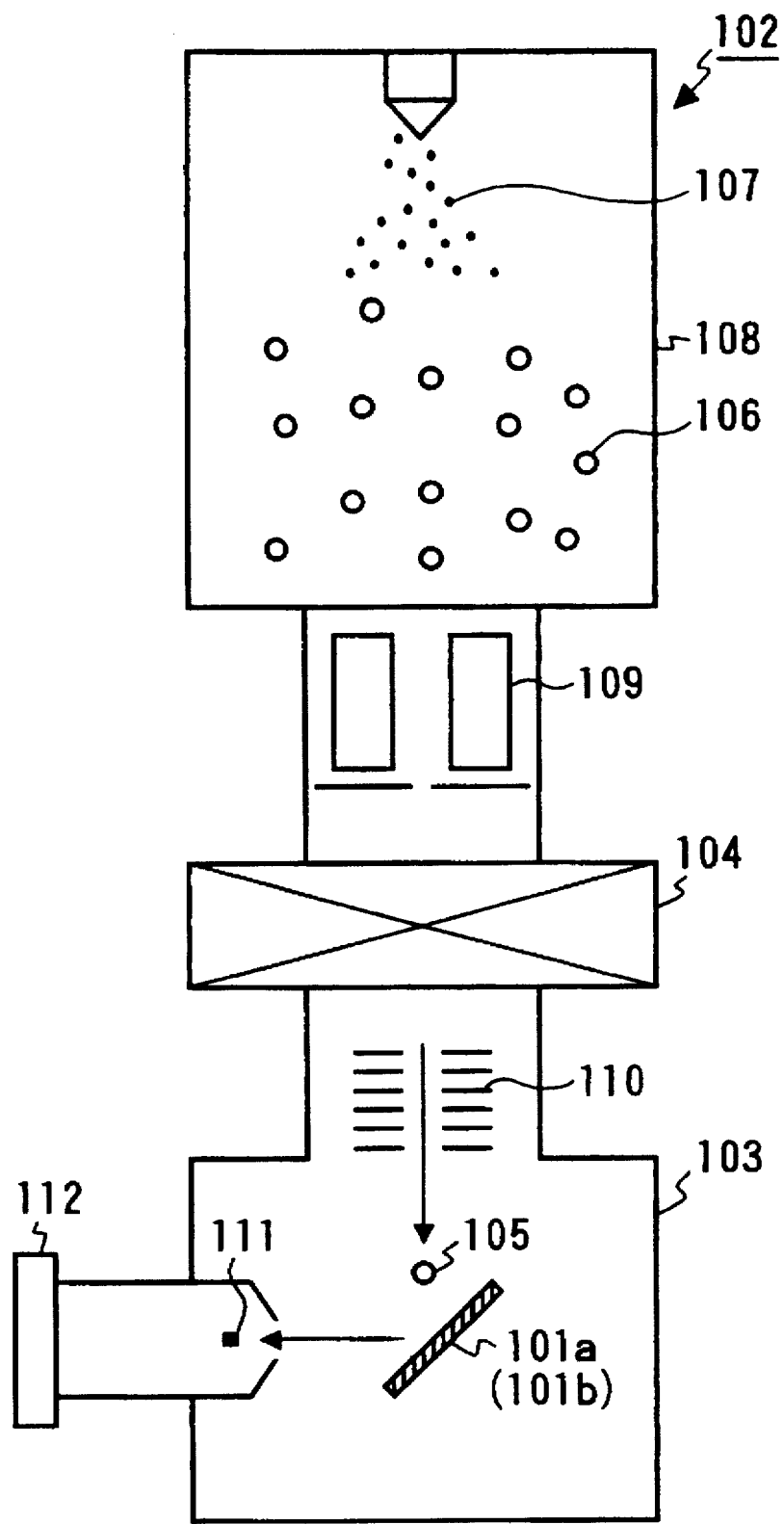
FIG. 1 is a view showing a schematic configuration of a surface measuring apparatus used for surface measurement in Embodiments 1 and 2 according to the present invention.

A first embodiment of the present invention will be described using FIG. 1. The present invention relates to an apparatus for Auger electron spectroscopy using a multiply-charged ion for excitation of a specimen surface.

An apparatus for multiply-charged ion excited Auger electron spectroscopy 102 according to the present embodiment comprises a multiply-charged ion source 108, a multiply-charged ion charge separator 109, a gate valve 104, an ion decelerator 110, a specimen chamber 103, an electron energy analyzer 112 and the like.

In the multiply-charged ion source 108, an electron beam 107 is irradiated on an introduced gas (Ar gas) to generate ions of various charges the multiply-charged ion charge separator 109 comprises a Wien filter, which separates only a multiply-charged ion having a specific charge from generated ions. The ion decelerator 110 decelerates a multiply-charged ion with the charge separated into a multiply-charged ion 105 of a low kinetic energy. The thus obtained multiply-charged ion 105 of specific charge and low kinetic energy is irradiated on the surface of a specimen 101a. The electron energy analyzer 112 measures a kinetic energy distribution of an electron 111 emitted from the surface of the specimen 101a by the irradiation of the multiply-charged ion 105.

The procedure for measurement is as follows. First, the specimen (in which an Si (100) substrate is immersed into a HF solution for 10 seconds, after which it is cleaned with pure water and dried) 101a is put into the specimen chamber 103. The specimen chamber 103 is evacuated to pressure not more than 5×10$^{-10}$ Torr. The gate valve 104 between the specimen chamber 103 and the multiply-charged ion charge separator (Wien filter) 109 is opened to irradiate the multiply-charged ion 105 on the specimen surface. In the multiply-charged ion source 108, the electron beam 107 of accelerated voltage 2 keV is irradiated on Ar gas 106 of pressure $1\times10^{-9}$ Torr to generate Ar ion ($Ar^+$). Out of the generated Ar ions ($Ar^+$) are separated and extracted, by the charge separator (Wien filter) 109, Ar ion with the charge state of 12 ($Ar^{12+}$)(a potential energy Ep emitted when capturing one electron=618.3 eV), Ar ion with the charge state of 13 ($Ar^{13+}$)(Ep=686.1 eV) and Ar ion with the charge state of 14 ($Ar^{14+}$)(Ep=755.8 eV), which are sequentially irradiated on the surface of the specimen 101a. At this time, the kinetic energy of the irradiated multiply-charged ion is adjusted to 20 eV using the ion decelerator 110. The kinetic energy distribution of an electron 111 emitted from the specimen surface by the irradiation of the multiply-charged ion was measured by the electron energy analyzer 112.

Figure 2:
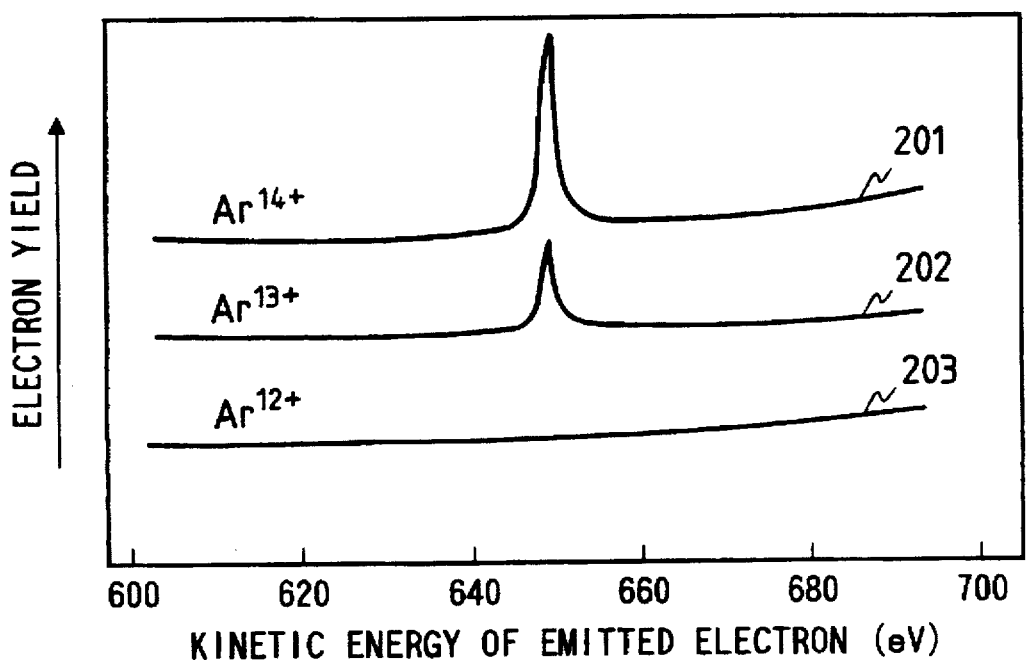
FIG. 2 is a view showing energy spectra of emitted electrons obtained as a result of surface measurement in Embodiment 1.

FIG. 2 shows the electron energy spectra obtained as a result of the above-described measurement. According to FIG. 2, peaks observed for electron energy spectra 201 and 202 when Ar ion with the charge state of 14 ($Ar^{14+}$) and Ar ion with the charge state of 13 ($Ar^{13+}$) are irradiated are in the vicinity of 650 eV whereas an electron energy spectrum 203 when Ar ion with the charge state of 12 ($Ar^{12+}$) is irradiated has no peak corresponding thereto observed.

The position of the peaks observed is very close to a kinetic energy value (647 eV) of Auger electron (F-KLL) from fluorine (F) atom. The minimum energy capable of ionizing a K-shell electron of the fluorine atom is 686 eV, and the above-described $Ar^{14+}$ and $Ar^{13+}$ ions can emit a potential energy having a value in excess thereof when capturing one electron. However, the $Ar^{12+}$ ion cannot emit a potential energy having a value in excess thereof. It has been found from the above-described result that the fluorine atom was present on the top surface layer of the specimen 101a. It is also found that there is a difference of approximately 3 eV between energy of emitted electron from the specimen surface and kinetic energy of Auger electron (F-KLL) from the fluorine (F) atom, and thus the fluorine atom is bonded with Si atom on the specimen surface. The reason is that the value of 3 eV corresponds to a chemical shift attributed to the bonding with Si atom of the fluorine atom.

The surface of the same specimen as that described above was measured by the Auger electron spectroscopy or the photo electron spectroscopy by way of the conventional irradiation of electron beam. No presence of fluorine atom was observed. The reason is that since the fluorine atom is present only on the top surface layer of the specimen (Si substrate) surface, the conventional measuring method failed to make detection because the measuring sensitivity relative to the top surface layer is low.

<EMBODIMENT 2>

A second embodiment of the present invention will be described using FIG. 1. In the present embodiment, a surface measurement of a specimen (GaAs (100) substrate) 101b which is different from that of Embodiment 1 was carried out using the apparatus for multiply-charged ion excited Auger electron spectroscopy 102 which is the same as that of the previous Embodiment 1.

First, there is prepared the specimen 101b in which a GaAs (100) substrate is immersed into a $H_2SO_4$-$H_2O_2$-$H_2O$ mixed solution (mixing ratio=4:1:1) for 10 seconds, after which it is cleaned with pure water and dried, and the specimen is put into the specimen chamber 103. After that, the specimen chamber 103 is evacuated to pressure not more than $5\times10^{-10}$ Torr, after which the specimen 101b is heated to 600° C. to decompose a native oxide film the specimen surface. Then, Ar ion with the charge state of 10 ($Ar^{10+}$) (Ep=48.7 eV), Ar ion with the charge state of 11 ($Ar^{11+}$) (Ep=539.0 eV), and Ar ion with the charge state of 12 ($Ar^{12+}$) (Ep=618.3 eV) are respectively removed and separated, and sequentially irradiated on the specimen surface, in a manner similar to the case of Embodiment 1. At this time, the kinetic energy of the irradiated multiply-charged ion 105 is adjusted to 20 eV, similarly to the case of Embodiment 1, using the ion decelerator 110. The kinetic energy distribution of an electron 111 emitted from the specimen surface by the irradiation of the multiply-charged ion is measured by the electron energy analyzer 112.

Figure 3:
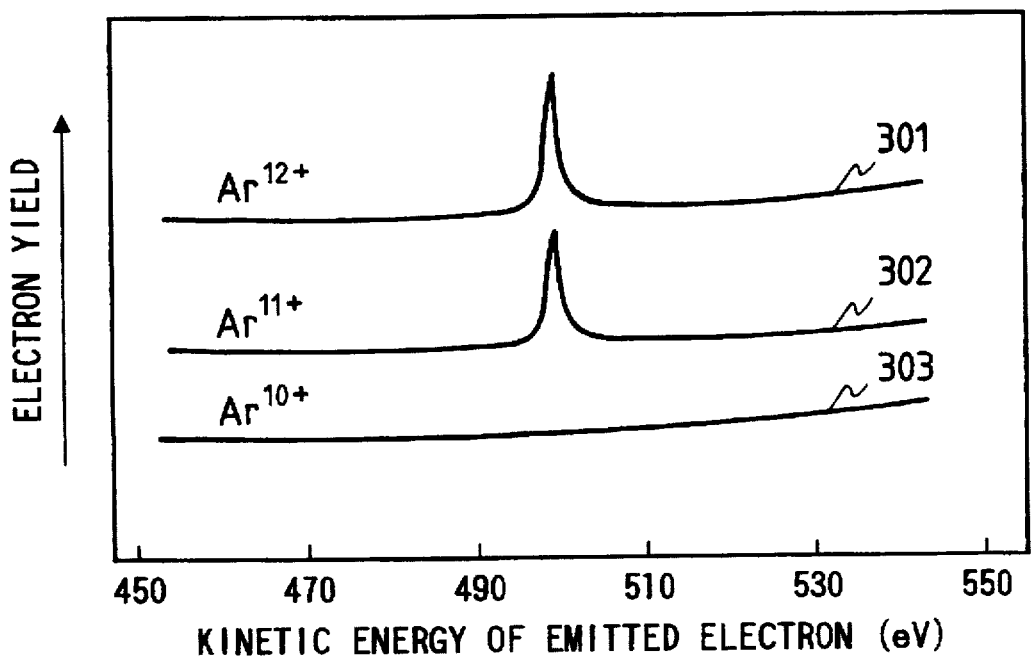
FIG. 3 is a view showing energy spectra of emitted electrons obtained as a result of surface measurement in Embodiment 2.

FIG. 3 shows the electron energy spectra obtained as a result of the above-described measurement. According to FIG. 2, peaks observed for electron energy spectra 301 and 302 when Ar ion with the charge state of 12 ($Ar^{12+}$) and Ar ion with the charge state of 11 ($Ar^{11+}$) are irradiated are in the vicinity of 500 eV whereas an electron energy spectrum 303 when Ar ion with the charge state of 10 ($Ar^{10+}$) is irradiated has no peak corresponding thereto observed. The position of the peaks observed is very close to a kinetic energy value (503 eV) of Auger electron (O-KLL) from oxygen (O) atom. The minimum energy capable of ionizing a K-shell electron of the oxygen atom is 532 eV, and the above-described $Ar^{11+}$ and $Ar^{12+}$ ions can emit a potential energy having a value in excess thereof when capturing one electron. However, the $Ar^{10+}$ ion cannot emit a potential energy having a value in excess thereof. It has been found from the above-described result that an oxygen atom is adsorbed on Ga atom of the top surface layer of the specimen 101b.

Generally, it is considered that the native oxide film of Ga in the specimen surface is decomposed/removed by heat treatment at 600° C. However, it has been found that by using the measuring method and apparatus according to the present invention, the oxygen atom still remains on the top surface layer even after the heat treatment.

<EMBODIMENT 3>

Figure 4:
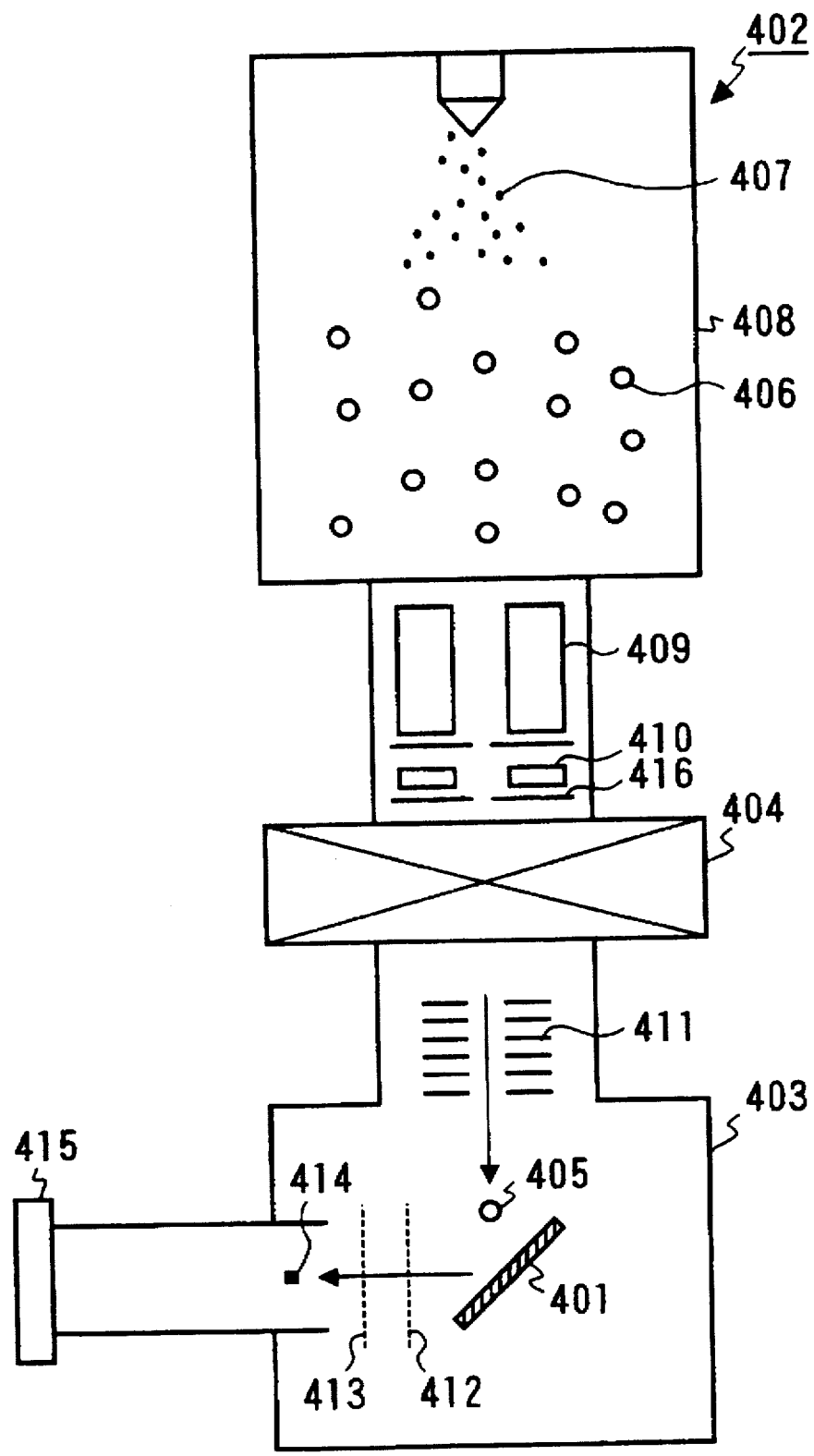
FIG. 4 is a view showing a schematic configuration of a surface measuring apparatus used for surface measurement in Embodiments 3 and 4 according to the present invention.

A third embodiment of the present invention will be described using FIG. 4. The present invention relates to a secondary ion mass analyzer using a multiply-charged ion for excitation of a specimen surface.

A multiply-charged ion excited secondary ion mass analyzer 402 according to the present embodiment comprises a multiply-charged ion source 408, a multiply-charged ion charge separator 409, an MCI pulse modulator 410, a slit 416, a gate valve 404, an ion decelerator 411, a specimen chamber 403, a sample grid 412, an acceleration grid 413, a time-of-flight (TOF) mass analyzer 415 and the like.

In the multiply-charged ion source 408, an electron beam 407 is irradiated on an introduced gas (Ar gas) 406 to generate ions of various charges. The multiply-charged ion charge separator 409 comprises a Wien filter, which separates and draws only a multiply-charged ion having a specific charge from the generated ions. The multiply-charged ion with the charge separated and drawn is deflected periodically whereby the multiply-charged ion passing through the slit 416 is subjected to pulse modulation. The ion decelerator 411 decelerates the multiply-charged ion subjected to the pulse modulation to form a pulse multiply-charged ion 405 having a low kinetic energy, after which the ion is irradiated on the surface of the sample 401. The time-of-flight mass analyzer 415 carries out the mass analysis of the secondary ion 414 emitted from the surface of the sample 401 by the irradiation of the pulse multiply-charged ion 105.

The procedure for measurement is as follows. First, there is prepared a sample (in which a Si (100) substrate is immersed in a 1% HF solution for 10 seconds, after which it is cleaned with pure water and dried) 401, and the sample 401 is put into a sample chamber 403. The sample chamber 403 is evacuated to pressure not more than $5 \times 10^{-10}$ Torr. In this state, the gate valve 404 is opened to irradiate the multiply-charged ion 40 on the sample surface. In the multiply-charged ion source 408, an electron beam 407 of acceleration voltage 5 keV is irradiated on Ar gas 406 of pressure $1 \times 10^{-9}$ Torr to generate Ar ion ($Ar^+$). Ar ion with the charge state of 18 ($Ar^{18+}$) (Ep=4426 eV) is separated and extracted from the generated Ar ion ($Ar^+$) by the charge separator (Wien filter) 409. Then, the multiply-charged ion passing through the slit 406 is subjected to pulse modulation (pulse width: 1 µs) in the pulse modulator 410, after which the multiply-charged ion 405 subjected to pulse modulation is irradiated on the surface of the sample 401. At this time, the kinetic energy of the multiply-charged ion 405 subjected pulse modulation irradiated on the sample is adjusted to 20 eV using the ion decelerator 411 provided within the sample chamber 403.

The same voltage as that of the sample 401 is applied to the sample grid 412, during the irradiation of the multiply-charged ion 405 subjected to pulse modulation (that is, during pulse width 1 µs, so that a space in the vicinity of the sample surface has the same potential as that of the sample surface). Within the time from the termination of the first irradiation of the pulse multiply-charged ion (irradiation time: 1 µs) to the time when next irradiation of the pulse multiply-charged ion begins (that is, time between pulse and pulse/non-irradiation time), the applied voltage to the sample grid 412 is lowered by 500 V than a sample potential, and the acceleration grid 413 is set to the same potential as-that of the sample grid 412 whereby the secondary ion 414 emitted from the surface of the specimen 401 is drawn into the time-of-flight mass analyzer 415 for mass analysis of the secondary ion 414.

Figure 5:
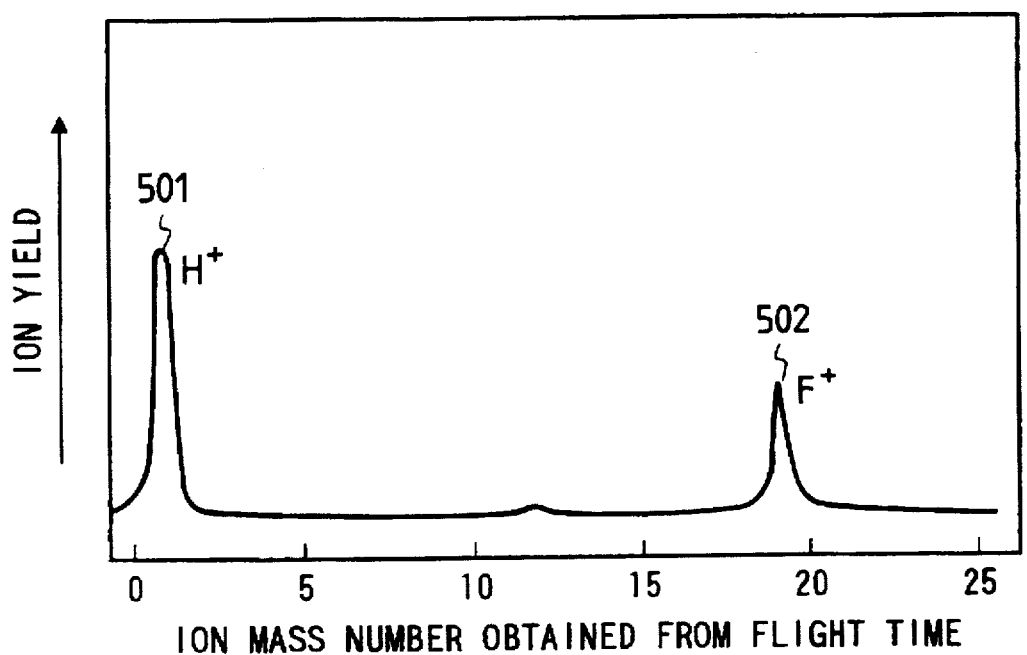
FIG. 5 is a view showing mass spectra of emitted ions obtained as a result of surface measurement in Embodiment 3.

FIG. 5 shows mass spectra of secondary ions obtained as a result of the mass analysis. According to FIG. 5, a peak 501 of hydrogen ion ($H^+$) with the charge state of 1 and a peak 502 of fluorine ion ($F^+$) with the charge state of 1 were observed at a position of mass number 1 and at a position of mass number 19, respectively. Thereby, it has been found that the hydrogen atom (H) and the fluorine atom (F) were present on the top surface layer of the sample.

For the purpose of comparison, the separating conditions of the Wien filter in the multiply-charged charge separator 409 are changed. Then, Ar ion ($Ar^+$) with the charge state of 1 (Ep=15.8 eV) is separated and taken out, which is then subjected pulse modulation (pulse width: 1 µs), and the kinetic energy is adjusted to 20 eV, after which it is irradiated on the sample 401. The mass analysis of the secondary ion emitted from the sample surface was conducted. In this case, however, neither peak of $H^+$ ion nor a peak of $F^+$ ion was observed.

It has been found therefrom that under the condition that the kinetic energy of the primary ion (excited ion) is low, the multiply-charged ion is utilized as the primary ion to thereby materially improve the measuring sensitivity.

Further, for the purpose of comparison, $Ar^+$ ion is used as the primary ion, and the kinetic energy is adjusted to 4430 eV (which is approximately the same as Ep value 4426 eV of $Ar^{18+}$ ion), under the condition of which the similar measurement was conducted. In that case, a peak of $H^+$ was slightly observed, but as compared with the case where $Ar^{18}$ + ion is used as the primary ion as previously mentioned, the peak value (yield of detection signal) was small by 4 digits or more. The peak of $F^+$ ion was neither observed. Thereby, it has been found that energy necessary for excitation of the secondary ion is given as a potential energy Ep rather than as a kinetic energy Ek of the exciting primary ion, which is more effective for improvement of the measuring sensitivity.

<EMBODIMENT 4>

A fourth embodiment of the present invention will be described using FIG. 4. The present embodiment uses the multiply-charged ion excited secondary ion mass analyzer 402 having the configuration of FIG. 4 which is the same as that of the previous Embodiment 3, whereby surface measurement (analysis of the primary ion mass) of the sample (Si (100) substrate) is conducted under the measuring conditions different from that of Embodiment 3 was conducted.

First, there is prepared a sample 401 in which a Si (100) substrate is immersed in a 1% HF solution for 10 seconds, after which it is cleaned with pure water and dried, and the sample 401 is put into a sample chamber 403. Subsequently, the sample chamber 403 is evacuated to pressure not more than $5 \times 10^{-10}$ ion with the charge state of 18 ($Ar^{18+}$) (Ep= 4426 eV) was separated and extracted, and then irradiated on the surface of the sample 401, in a manner similar to that of Embodiment 3. The measuring conditions of this embodiment is different from that of Embodiment 3 in that a pulse width of a pulse deflection voltage applied to an electrostatic deflector in the multiply-charged ion pulse modulator 410 is shortened, and an opening width of the slit 416 is made as narrow as possible, whereby a pulse width of the multiply-charged ion passing through the slit 416 is shortened to 100 ns so that the resolution in the time-of-flight mass analyzer 415 is higher than that of Embodiment 3. At this time, the kinetic energy of the multiply-charged ion ($Ar^{18+}$) is adjusted to 20 eV, similar to Embodiment 3, making use of the ion decelerator 411 within the sample chamber 403. The secondary ion 414 emitted from the surface of the sample 401 by the irradiation of the multiply-charged ion 405 was drawn into the time-of-flight mass analyzer 415 for mass analysis, in a manner similar to that of Embodiment 3.

Figure 6:
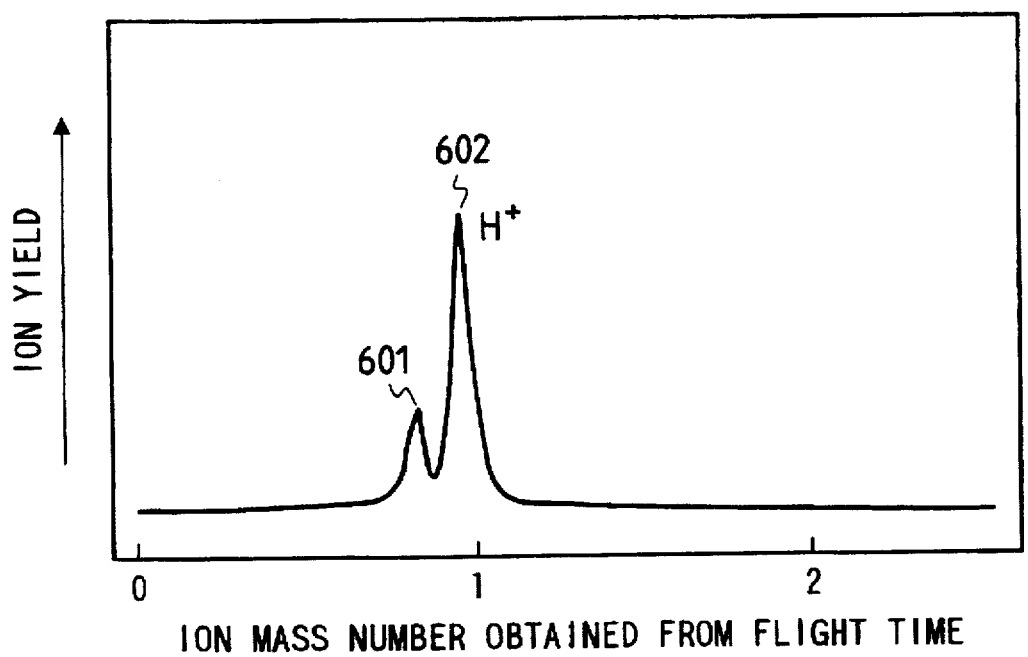
FIG. 6 is a view showing mass spectra of emitted ions obtained as a result of surface measurement in Embodiment 4.

FIG. 6 shows mass spectra of a portion of hydrogen ion ($H^+$) having a mass number 1 out of mass spectra of the secondary ion 414 obtained as a result of the above-described mass analysis. Signal of the $H^+$ ion was observed at a position of the mass number 1. However, in more detail, it was understood that the signal was split into two peaks. It is understood from the foregoing that two different components of a large component 601 and a small component 602 of the initial kinetic energy when $H^+$ ion is emitted from the sample surface were present and that two kinds of the bonding states of hydrogen atoms in the sample surface were present. For the purpose of confirmation, mass spectra for portions of other mass number were carefully observed, as a result of which as illustrated in Embodiment 3, a signal peak of $F^+$ ion was observed at a position of mass number 19 and a signal peak of $C^+$ ion was observed at a position of mass number 12.

On the other hand, with respect to the sample (Si substrate) before being subjected to fluorine treatment whose surface seems to be covered with many hydrocarbon contaminations, mass spectra of the secondary ion emitted from the sample surface when the multiply-charged ion ($Ar^{18+}$) is irradiated. As a result, a peak of $C^+$ ion whose yield is larger by about 1 digit than the sample after being subjected to fluorine treatment as previously mentioned was observed. At the same position as the component 601 which is large in initial kinetic energy shown in FIG. 6, a peak of $H^+$ whose yield is larger by one digit than that shown in FIG. 6 was observed, but at a position of the component 602 whose initial kinetic energy is small, a peak of $H^+$ was not observed.

Figure 13:
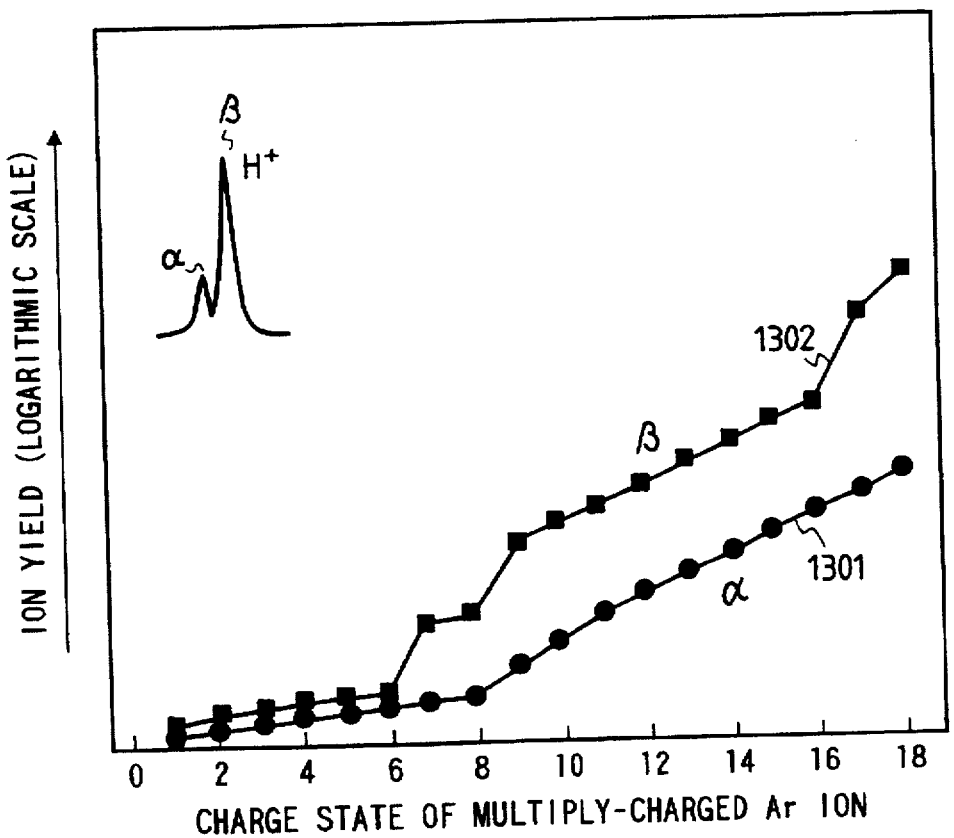
FIG. 13 is a view showing a dependability of a yield of the emitted ion with respect to the charge state of irradiated ions obtained as a result of experiment in Embodiment 4.

In a manner similar to Embodiments 1 and 2, the charge state dependence of signal yields of the component 601 whose initial kinetic energy is large and the component 602 whose initial kinetic energy is small was examined using $Ar^+$ ions different in the charge state. FIG. 13 shows a charge state dependence 1301 of a component α whose initial kinetic energy is large and a charge state dependence 1302 of a component β whose initial kinetic energy is small. It was found that the yield of the component α whose initial kinetic energy is large rapidly increased when the charge state of the irradiated ion changes from the charge state of 8 (Ep=143.5 eV) to the charge state of 9 (Ep=422.5 eV) whereas the yield of the component β whose initial kinetic energy is small rapidly changes when the charge state of the irradiated ion changes from the charge state of 6 (Ep=91.0 eV) to the charge state of 7 (Ep=124.3 eV), from the charge state of 8 (Ep=143.5 eV) to the charge state of 9 (Ep=422.5 eV), and from the charge state of 16 (Ep=918.0 eV) to the charge state of 17 (Ep=41.21 eV), respectively. The minimal energy capable of ionizing the K-shell electron of C-atom is 284 eV, which corresponds to that when the irradiated ion changes from the charge state of 8 to the charge state of 9. The minimum energy capable of ionizing the L-shell $2p$ electron of Si atom is 100 eV, the minimum energy capable of ionizing the L-shell $2s$ electron of Si atom is 149 eV, and the minimum energy capable of ionizing the K-shell electron is 1839 eV. These correspond to those in which the charge state of the irradiated ion changes from the charge state of 6 to 7, from the charge state of 8 to 9, and from the charge state of 16 to 17.

It was found from these results that two peaks of a signal of H ion in FIG. 6 are that the component 601 (α in FIG. 13) whose initial kinetic energy is large results from C-H bonding attributed to carbon present in the surface whereas the component 602 (β in FIG. 13) whose initial kinetic energy is small results from Si-H coupling attributed to silicone of a substrate exposed to the surface by the fluorine treatment.

For the purpose of comparison, the sample after the fluorine treatment and the sample before the fluorine treatment were examined using $Ar^+$ ion with the charge state of one, whose kinetic energy is 4430 eV (which is approximately the same as Ep value of $Ar^{18+}$ ion with the charge state of 18) as the primary ion. A signal of $H^+$ was obtained as the secondary ion, but the signal yield is small by 4 digits or more as compared with the case where $Ar^{18+}$ ion is used as the primary ion, and the splitting of signal peaks as mentioned above was not observed.

As described above, by using the multiply-charged ion as the primary ion, the measuring sensitivity can be materially improved as compared with the case where the accelerated ion with the charge state of 1, and in addition, by the analysis of the initial kinetic energy of the emitted particles (secondary ions), the difference of the bonding state of atoms in the sample surface can be examined.

<EMBODIMENT 5>

Figure 7:
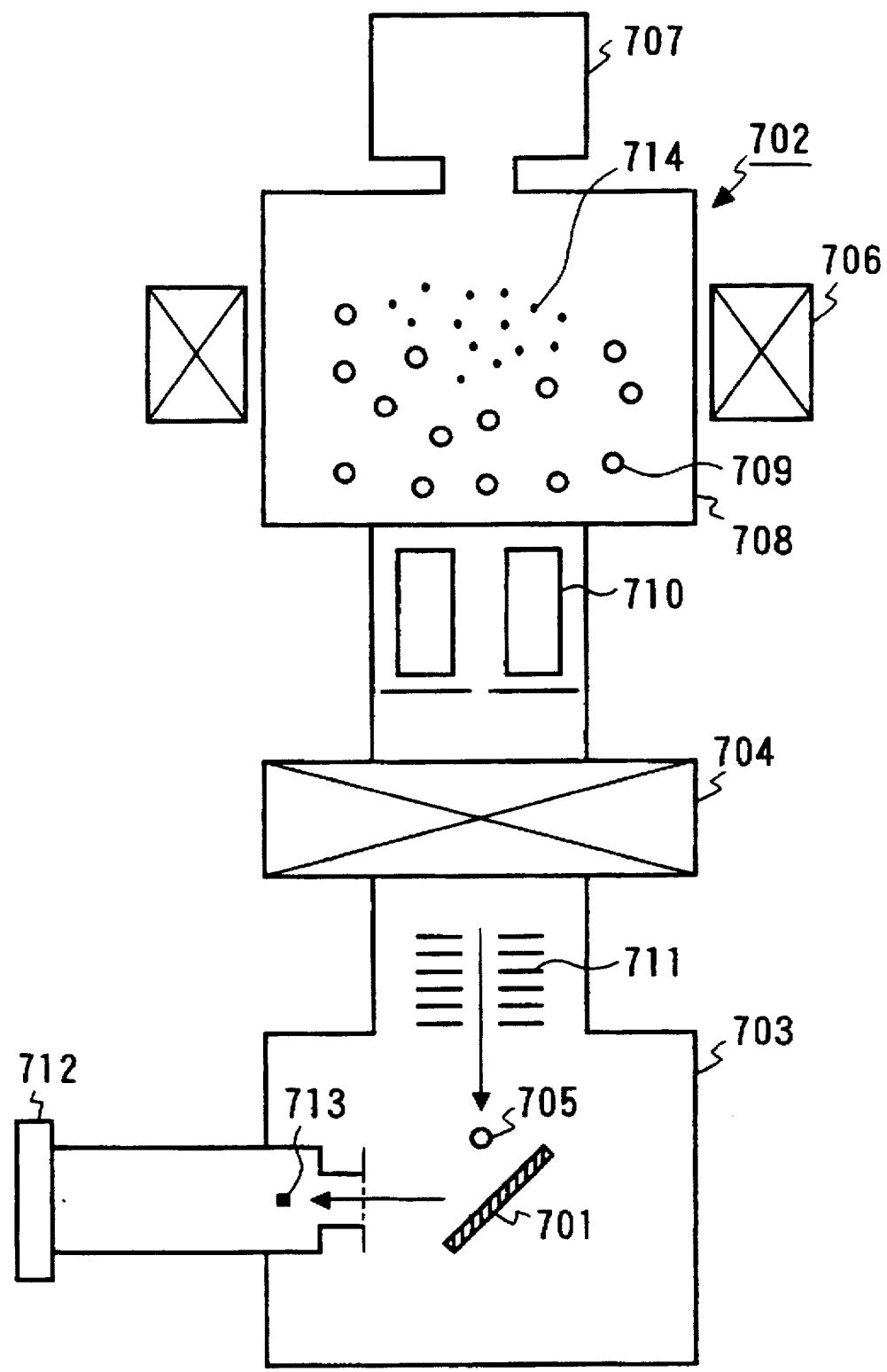
FIG. 7 is a view showing a schematic configuration of a surface measuring apparatus used for surface measurement in Embodiment 5 according to the present invention.

A fifth embodiment of the present invention will be described using FIG. 7. In the present embodiment, a multiply-charged excited secondary ion mass analyzer 702 is used to carry out surface measurement (analysis of secondary ion mass) of a sample (GaAs (100) substrate) 701.

First, there is prepared, as the sample 701, a GaAs (100) substrate which is immersed in a $H_2SO_4$-$H_2O_2$-$H_2O$ mixed solution (a mixing ratio=4:1:1) for 10 seconds, after which it is cleaned with pure water and dried, and the sample is put into a sample chamber 703. Subsequently, the sample chamber 703 is evacuated to pressure not more than $5 \times 10^{-10}$ Torr, and after this, the sample 701 is heated to 600° C. to decompose a native oxide film on the sample surface. At this time, the sample surface becomes a Ga-terminated surface. Next, a gate valve 704 between the sample chamber 703 and the multiply-charged ion charge state separator 710 is opened to irradiate a multiply-charged ion 705 on the surface of the sample 701. A plasma 714 is generated by a solenoid coil 706 and a micro-wave generator 707 provided on a multiply-charged ion source 708 to generate Ar ion as a raw material gas. $Ar^{16+}$ ion with the charge state of 16 (Ep=918.0 eV) 705 is extracted as a continuous beam from the generated Ar ion by a charge state separator 710 (Wien filter), and the beam was irradiated on the surface of the sample 701.

The quantity of multiply-charged ions generated from a multiply-charged ion source of a microwave plasma excitation type is extremely large as compared with the electron excitation type used in the previous embodiments. Therefore, in order to prevent the measured results from being affected by the thermal reaction, the sample 701 was cooled to prevent the sample from being raised in temperature due to the irradiation of ions. Further, an ion decelerator 711 was used to adjust the kinetic energy of the irradiated multiply-charged ion to 20 eV. A potential difference of 50 V is provided between the sample 701 and an inlet of a quadruple mass analyzer 712 so that a secondary ion 713 emitted from the sample surface is drawn into the quadruple mass analyzer 712 for mass analysis thereof.

Figure 8:
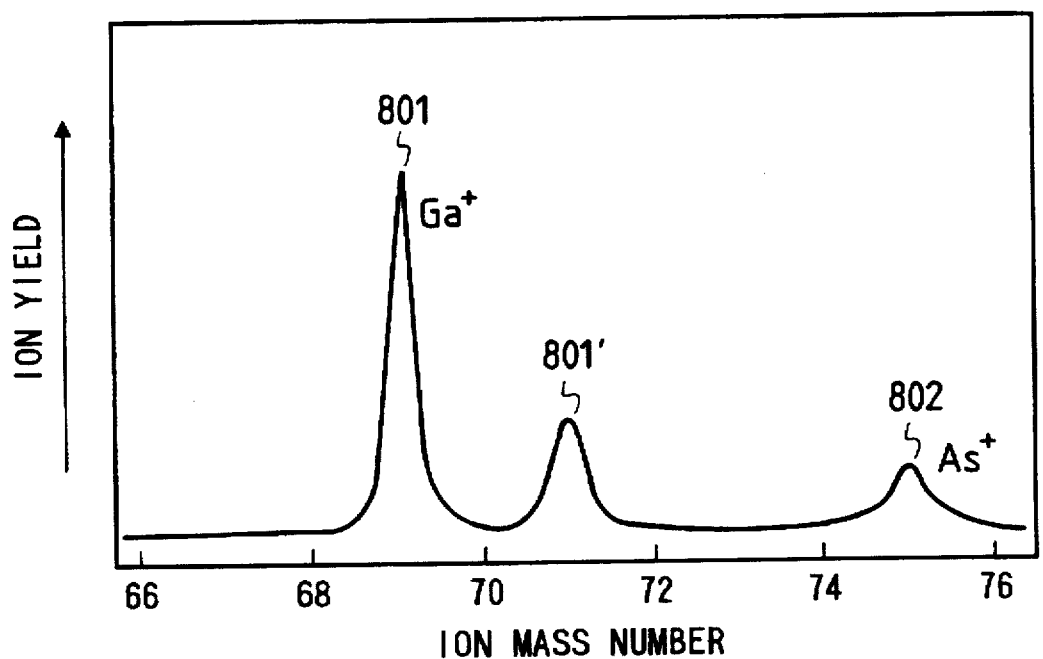
FIG. 8 is a view showing mass spectra of emitted ions obtained as a result of surface measurement in Embodiment 5.
Figure 9:
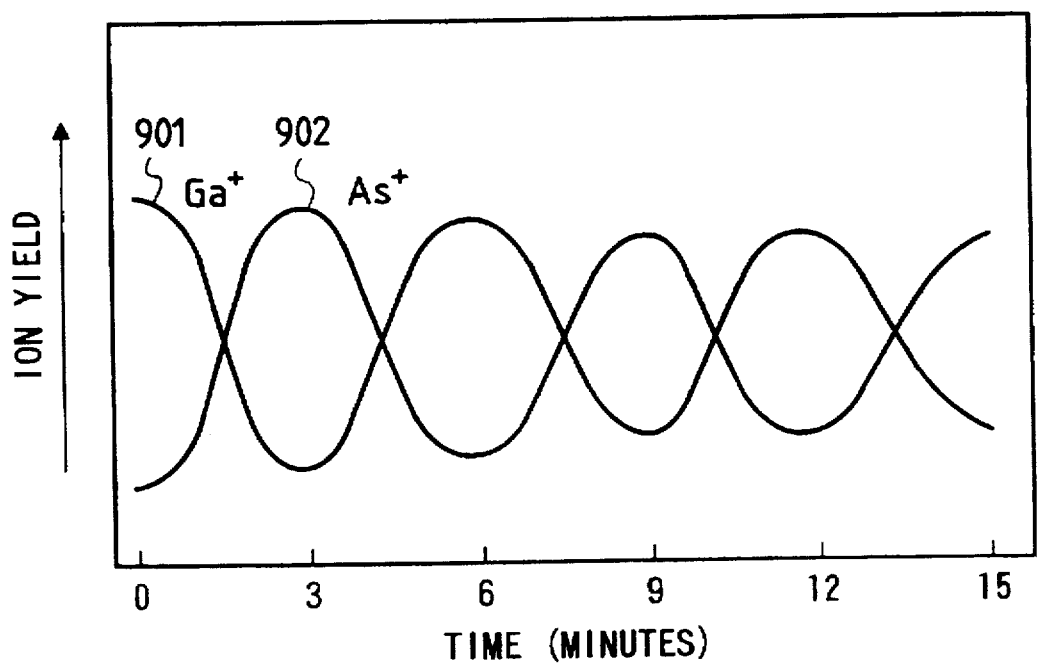
FIG. 9 is a view showing a change of a lapse of time of peak yields of Ga$^+$ ion and As$^+$ ion out of mass spectra of emitted ions obtained as a result of surface measurement in Embodiment 5.

FIG. 8 shows mass spectra of ions obtained as a result of the mass analysis. According to FIG. 8, a signal 801 of Ga ion ($Ga^+$) with the charge state of 1, a signal 801' of isotope ion, and a fine amount of a signal 802 of As ion ($As^+$) with the charge state of 1 were observed at a position of mass number 69, at a position of mass number 71 and at a position of mass number 75, respectively. Attention was paid merely to a signal peak of ($Ga^+$) at a position of mass number 69 and a signal peak of $As^+$ at a position of mass number 75, and a change of a lapse of time of the peak signal yield of two signal peaks was examined while irradiating $Ar^{16+}$. The obtained results are shown in FIG. 9. At the time of starting measurement, a signal yield 901 of $Ga^+$ was stronger than a signal yield 902 of $As^+$ but as the measurement proceeds, the signal yield 901 of $Ga^+$ gradually reduced whereas the signal yield 902 of $As^+$ gradually increased. After passage of 3 minutes after the start of measurement, the relationship of yield therebetween is nearly inverted. Thereafter, when the measurement continues, then the signal yield 901 of $Ga^+$ gradually increased whereas the signal yield 902 of $As^+$ gradually reduced. As a result of continuation of such measurement for 15 minutes, the state where the relationship of yield therebetween is replaced every 3 minutes was observed as shown in FIG. 9. This data was obtained by observing the particles (secondary ions) emitted from the sample while continuously performing etching of the sample surface by the irradiation of the multiply-charged ion, which shows, so-called, the distribution of Ga element and As element widthwise from the sample surface.

Figure 10:
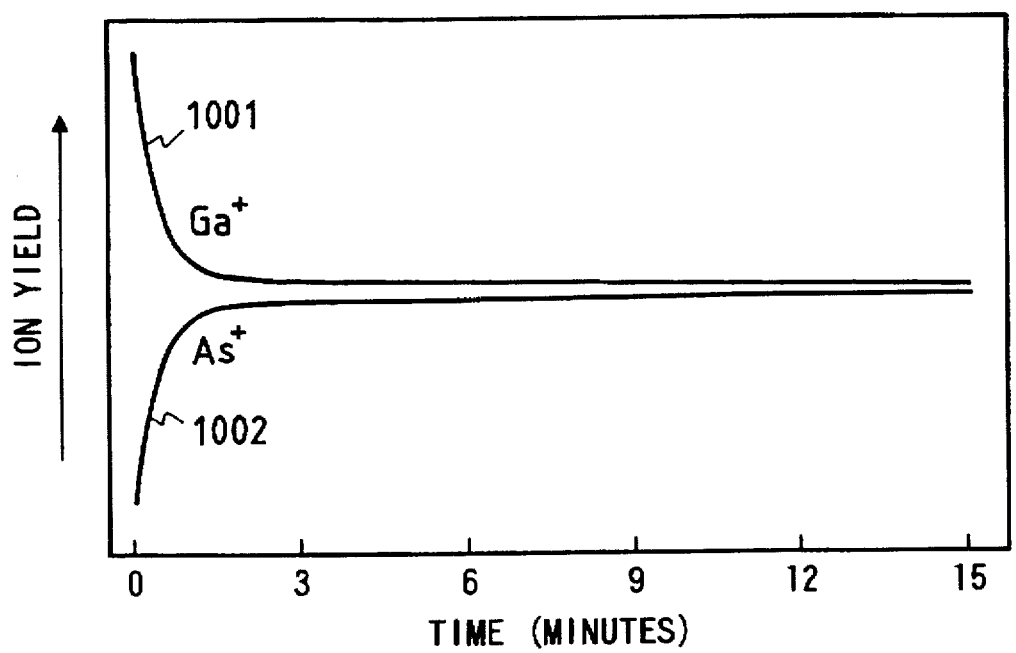
FIG. 10 is a view showing a change of a lapse of time of peak yields of Ga$^+$ ion and As$^+$ ion among mass spectra of emitted ions obtained when a single-charged Ar ion is irradiated on the specimen surface, for the purpose of comparison, in Embodiment 5.

For the purpose of comparison, the secondary ion emitted from the sample was examined while continuously irradiating Ar ion (Ar$^+$) with the charge state of 1 whose kinetic energy is 920 eV (which is nearly the same value as Ep value of Ar$^{16+}$) on the same sample as that described above. The obtained results are shown in FIG. 10. At the time of starting the measurement, a signal yield 1001 of Ga$^+$ was larger than a signal yield 1002 of As$^+$ but the signal yield 1001 of Ga$^+$ gradually reduced, whereas the signal yield 1002 of (As$^+$) gradually increased. After the passage of about 2 minutes after start of measurement, both the signal yields were settled at substantially same constant levels. When such a measurement was continued for 15 minutes, no inverted phenomenon of the yield relationship between both the signals which has been observed in the case that Ar$^{16+}$ ion has been irradiated with deceleration was observed but the yields of both the signals were finally constant.

It was found from the above-described results that in the case that the decelerated multiply-charged ion is utilized, the depth distribution of elements could be measured with the resolution at levels of atom layer while proceeding etching at levels of atom layer, with respect to the sample in which Ga atom layer and As atom layer are alternately stacked each other. On the other hand, in the case that the accelerated ion with the charge state of 1 is utilized, etching proceeds with the disturbance of lattice structure from a few to scores of layers at least from the sample surface, as a result of which the depth-distribution of elements cannot be measured with the depth resolution at levels of atom layer. Further, in other words, this indicates that in the measurement of the depth distribution using the accelerated ion as in the conventional secondary ion mass analyzing method, the lattice structure of the underlying layer is destroyed to give a damage, whereas in the case that the decelerated multiply-charged ion is used, the damage given to the lattice structure of the underlying layer is less than one atom layer.

<EMBODIMENT 6>

A sixth embodiment of the present invention will be described using FIG. 7. In the present embodiment, the same multiply-charged ion excited secondary ion mass analyzer 702 as that of the previous embodiment 5 is used to carry out the surface measurement (secondary ion mass analysis) of a sample (Si (100) substrate with a boron element delta-doped) 701.

First, there is prepared the sample 70, in which a Si (100) substrate 701 formed with a delta-doped layer of boron at a position of depth of 100 nm from the surface is immersed in a 1% HF solution for 10 seconds, after which it is cleaned with pure water and dried, and the sample 701 is put into a sample chamber 703. Then, the sample chamber is evacuated to pressure not more than 5×10$^{-10}$ Torr. Under the same method and condition as those shown in Embodiment 5, Ar ion (Ar$^{16+}$) with the charge state of 16 (Ep=918.0 eV) 705 is extracted as a continuous beam, which was irradiated on the surface of the sample 701. Further, the sample was cooled to prevent the sample from being raised in temperature due to the irradiation of ion, similarly to the case of Embodiment 5. The kinetic energy of the irradiated multiply-charged ion 705 was adjusted to 20 eV using the ion decelerator 711. A potential difference of 50 V is provided between the sample 701 and an inlet of the quadruple mass analyzer 712 so that an ion 713 emitted from the sample surface is drawn into the quadruple mass analyzer 712 for mass analysis.

Figure 11:
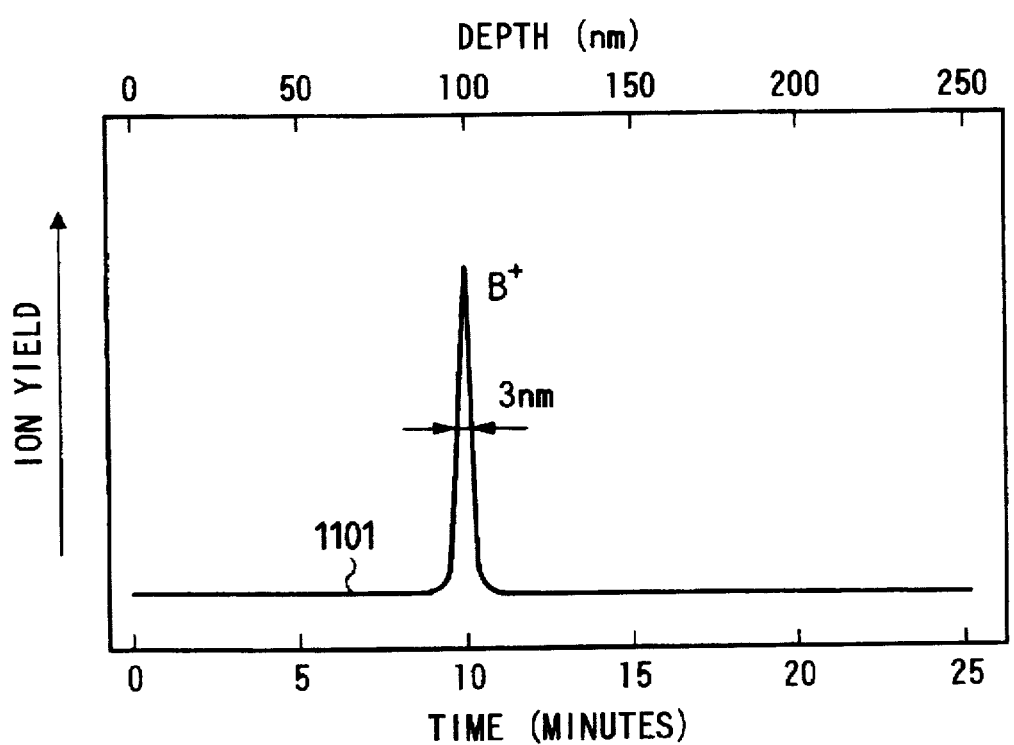
FIG. 11 is a view showing a change of a lapse of time (corresponding to the depth distribution of B atom) of the yield of an emitted B$^+$ ion obtained as a result of surface measurement in Embodiment 6.

As mentioned in previous Embodiment 5, the secondary particles emitted from the sample are observed (mass analyzed) while continuously performing etching of the sample surface by the irradiation of the multiply-charged ion whereby to obtain the distribution of elements widthwise from the sample surface. Attention is paid merely to a signal peak of a boron ion (B$^+$) with the charge state of 1 at a position of mass number 11 in order to analyze the depth distribution of boron (B) which is a dopant, and a change of a lapse of time of a signal yield of B$^+$ ion was examined while irradiating Ar$^{16+}$. The obtained results are shown in FIG. 11. A signal yield change curve 1101 of B$^+$ obtained using a multiply-charged ion shows the distribution of boron atom (B) widthwise from the sample surface as it is. After the passage of 10 minutes after the start of measurement, the signal yield of B$^+$ ion shows its maximum value. The position showing the maximum value corresponds to the depth position of 100 nm from the sample surface. Further, when the spread of the depth distribution of boron atom (B) is obtained from FIG. 11, it was found to be 3 nm with half value width.

Figure 12:
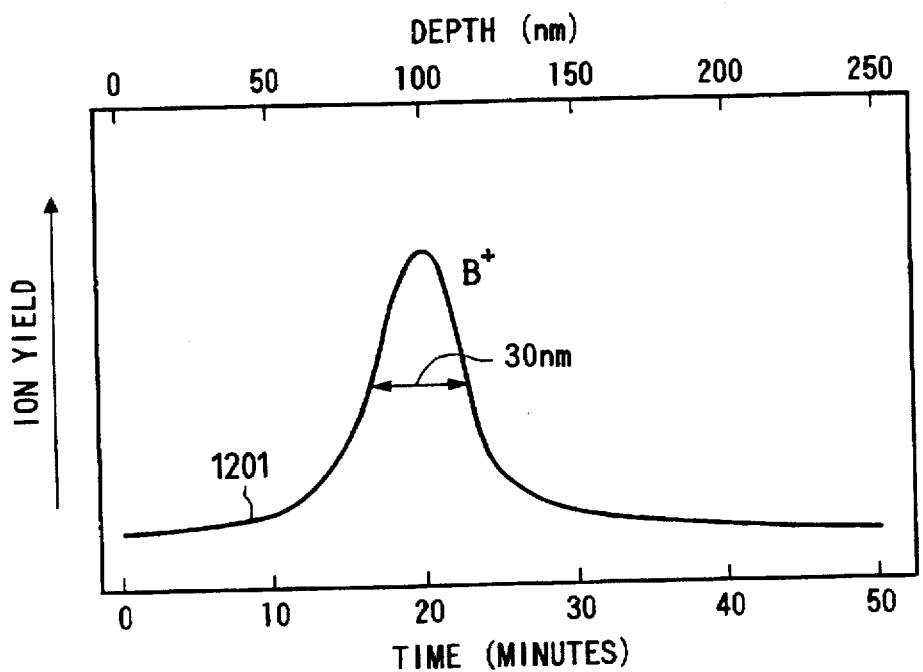
FIG. 12 is a view showing a change of a lapse of time of the yield of an emitted B$^+$ ion obtained when an accelerated single-charged Ar ion is irradiated on the specimen surface, for the purpose of comparison, in Embodiment 6.

For the purpose of comparison, a change of a lapse of time of the signal yield of B$^+$ emitted from the sample was examined while continuously irradiating Ar ion (Ar$^+$) with the charge state of one accelerated to kinetic energy 920 eV (which is nearly the same value as Ep value of Ar$^{16+}$) on the same sample as that mentioned above. The obtained results are shown in FIG. 12. A depth distribution curve 1201 obtained using the accelerated ion showed that the signal yield of B$^+$ after the passage of 20 minutes after the start of measurement is maximum. This position showing the maximum corresponds to the depth position of about 100 nm from the sample surface. When the spread of the depth distribution of boron atom (B) is obtained from FIG. 12, indicated is the larger spread width than actual spread by one digit, 30 nm with half value width, being different from the case of FIG. 11 previously mentioned. This indicates that in the measurement using an accelerated ion with the charge state of 1 as a primary ion, the sample surface is measured while etching it by the dynamic sputtering, and therefore, the disturbance of lattice structure brought by the ion irradiation into a crystal extends to the depth of at least scores of atom layers, as a result of which it was not possible to obtain the depth resolution such that an extremely thin (say, 3 nm) dope layer can be measured accurately. On the other hand, in the measurement using a multiply-charged ion as a primary ion according to the present invention, the multiply-charged ion is decelerated to 20 eV and then irradiated on the sample, and therefore, the ion irradiation does not cause the disturbance of lattice structure into the crystal, etching can proceed per atom layer from the top surface layer, and the measurement with high depth resolution becomes possible.

As described above, by the measurement of the depth distribution using the multiply-charged ion according to the present embodiment, it was confirmed that for the objective sample, an extremely thin (thickness is 3 nm) dope layer is formed at a position of depth 100 nm from the sample surface was formed. The measuring method and apparatus for a depth profile using the multiply-charged ion mentioned in the present embodiment can be widely applied, other than such a delta-doped sample, to fields which require high precision measurements for the depth profile, such as evaluation of a ultra shallowly doped sample, and measurements of an acute interface of an oxide film of a semiconductor surface, a nitride film, a multiple-layer evaporated film, a super lattice and the like.

<EMBODIMENT 7>

Figure 15:
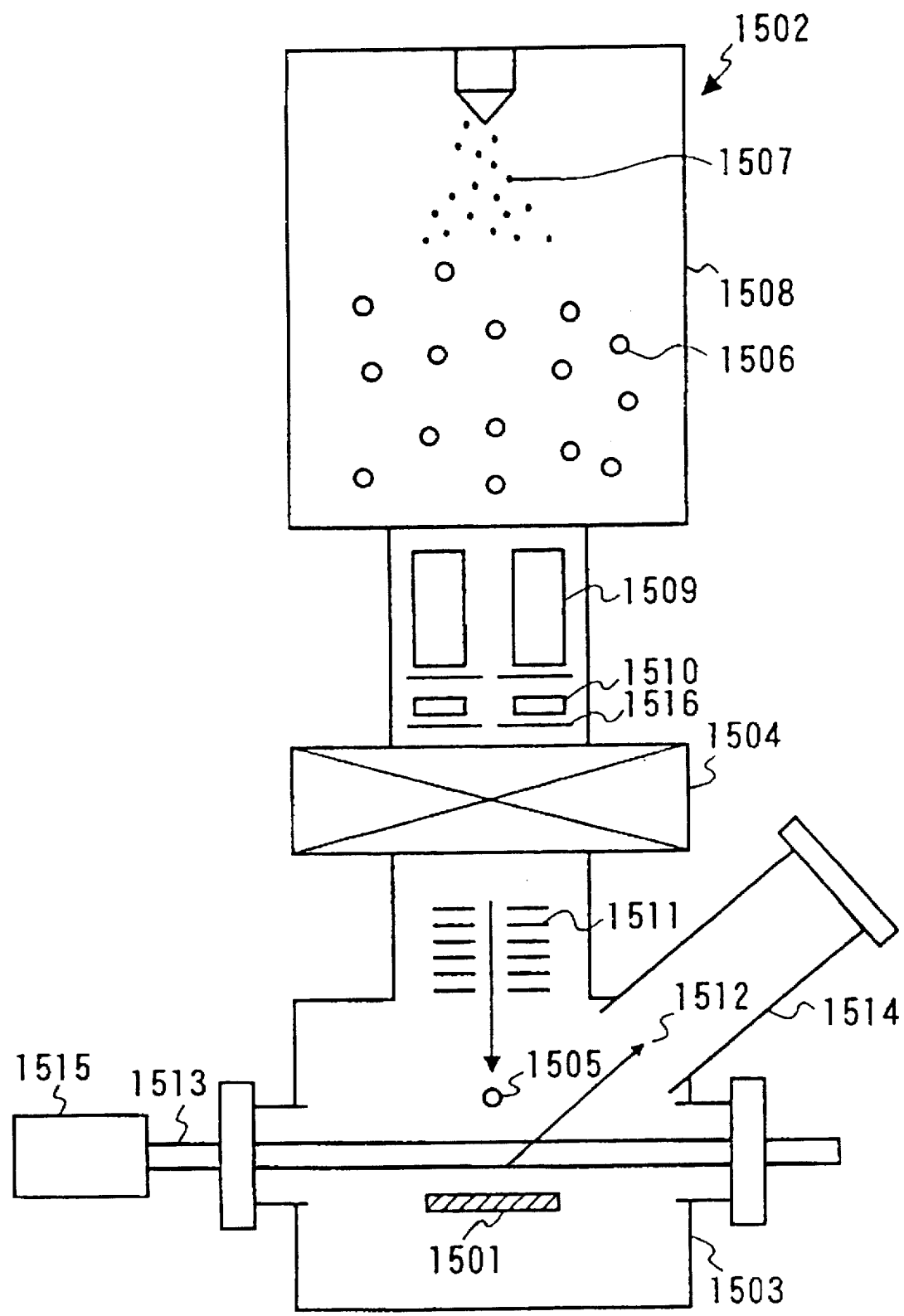
FIG. 15 is a view showing a schematic configuration of a surface measuring apparatus used for surface measurement in Embodiment 7 according to the present invention.

A seventh embodiment of the present invention will be described using FIG. 15. In the present embodiment, a multiply-charged ion excited neutral particle mass analyzer 1502 is used to perform a surface measurement of a sample (a compound semiconductor multilayer film).

Figure 16:
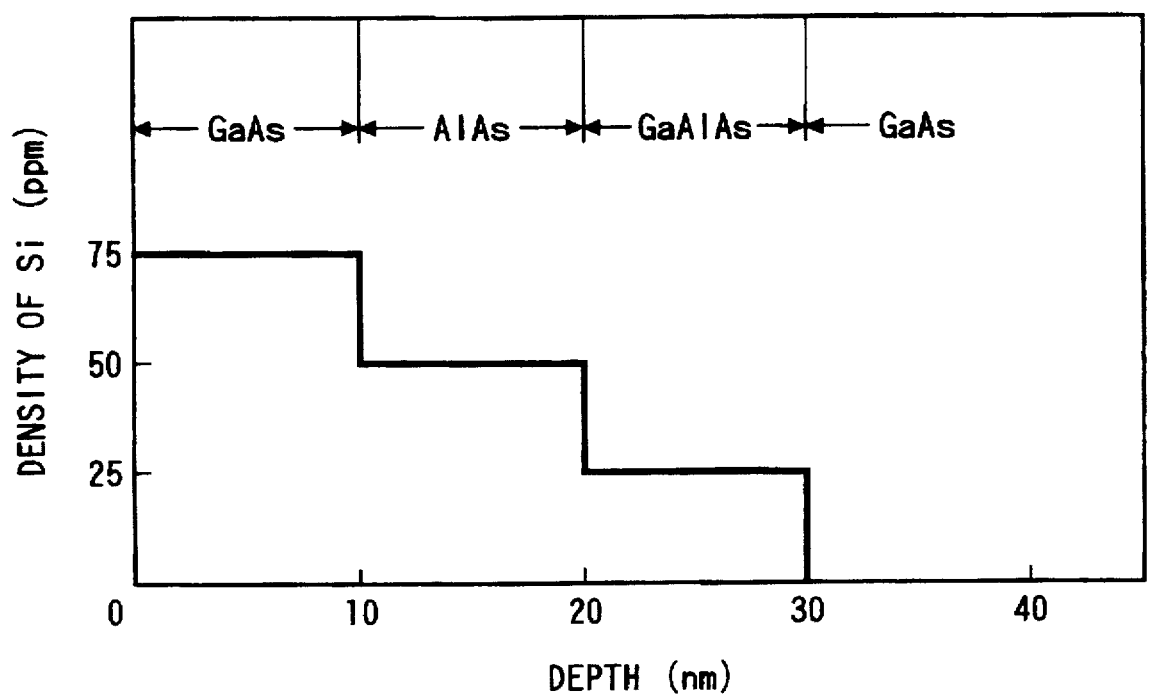
FIG. 16 is a view showing a depth distribution of concentration of Si atom obtained as a result of surface measurement in Embodiment 7.
Figure 17A:
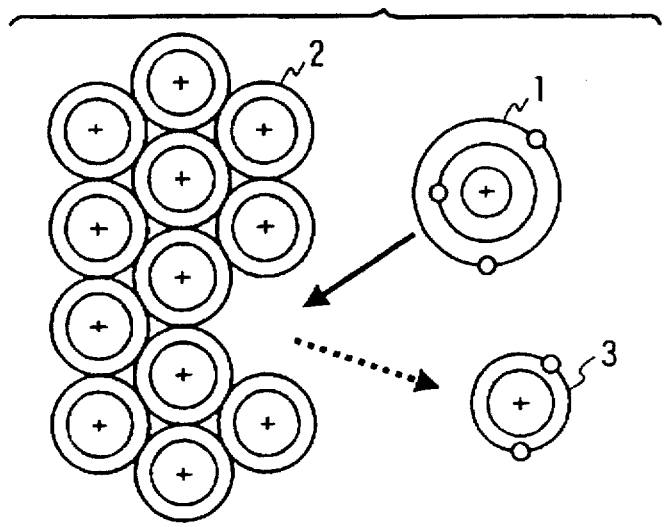
FIGS. 17A and 17B show a view and graph for explaining an interaction between a multiply-charged ion and a solid surface.
Figure 17B:
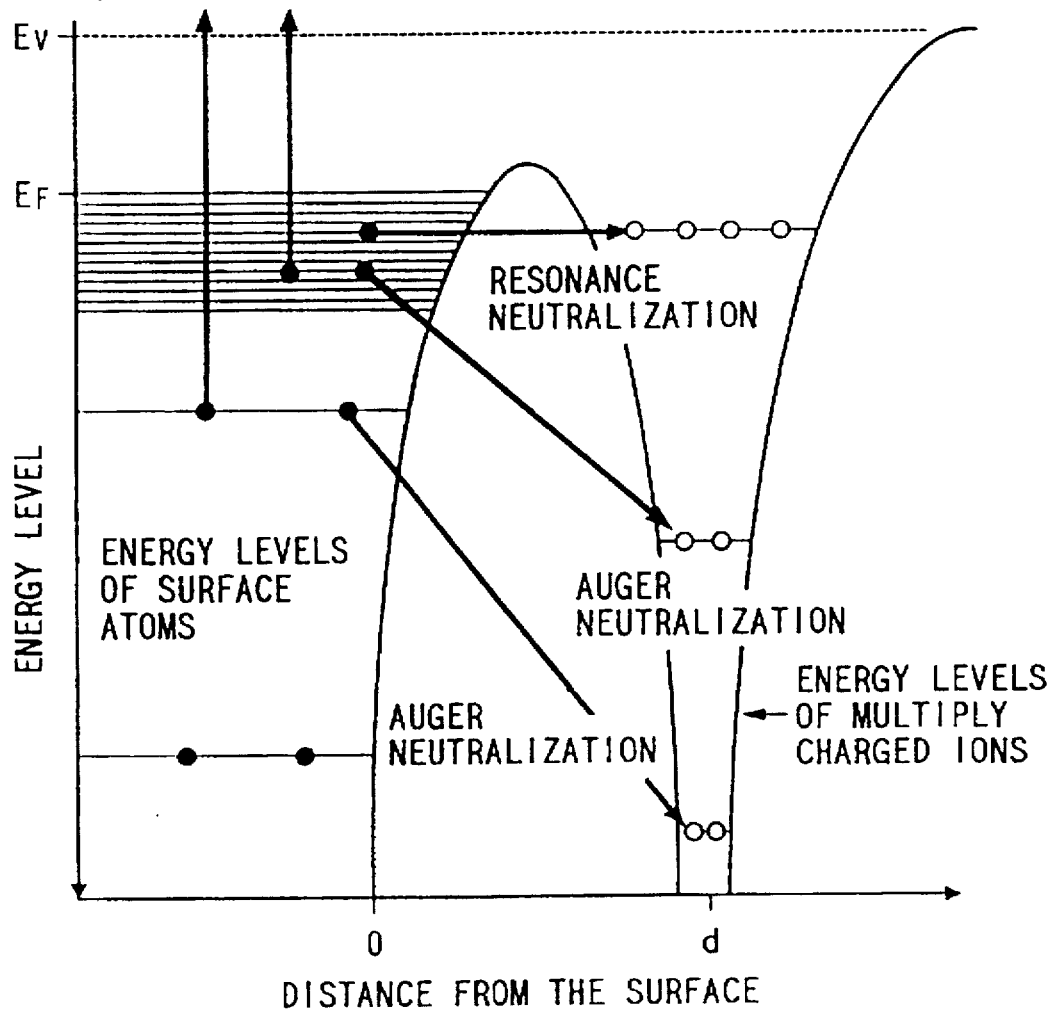

The sample 1501 in the present embodiment is formed in a manner such that by way of a molecular beam epitaxy method, a GaAlAs layer, an AlAs layer, and a GaAs layer are sequentially stacked on a GaAs substrate, and Si in amount of 25 ppm, 50 ppm and 75 ppm, respectively, is mixed into the respective layers. This sample is put into a sample chamber 1503 of the multiply-charged ion excited neutral particle mass analyzer 1502, and the sample chamber is evacuated to pressure not more than $5 \times 10^{-10}$ Torr. Next, a gate valve 1504 between the sample chamber 1503 and a multiply-charged ion charge state separator 1509 is opened to irradiate a multiply-charged ion 1505 on the surface of the sample 1501. In a multiply-charged source 1508, an electron beam 1507 of accelerated voltage 5 ke V is irradiated on Ar gas 1506 of pressure $1 \times 10^{-9}$ Torr to generate Ar ions with various charge states. A multiply-charged Ar ion ($Ar^{18+}$) with the charge state of 18 (Ep=4426 eV) is separated and extracted from the generated Ar ion using a charge state separator (Wien filter) 1509. The extracted $Ar^{18+}$ ion is subjected to pulse modulation (pulse width: 1 µs) using a deflector 1510 and a slit 1516 (slit width: 3 mm) formed directly thereafter, and the ion subjected to pulse modulation was irradiated on the sample surface. At this time, the kinetic energy of the irradiated ion ($Ar^{18+}$) was adjusted to 20 eV using an ion decelerator 1511 within the sample chamber. Immediately after the multiply-charged ion pulse has been irradiated, a laser beam 1513 radiated from a laser device 1515 was irradiated so as to pass through a space immediately above the surface of the sample 1501. In the irradiation of the laser beam to the space immediately above the sample surface, that is, the space between the sample 1501 and the ion decelerator 1511, it is important to consider that the laser beam 1513 was irradiated in the direction substantially parallel with the surface of the sample 1501 so that the laser beam does not directly impinge upon the sample surface. By the irradiation of the laser beam, the neutral particles emitted from the sample surface by the previous irradiation of the multiply-charged ion are ionized with the probability of nearly 100%. This ion 1512 is detected by a mass analyzer 1514 to thereby enable the element analysis of the sample surface. The above-described multiply-charged ion and laser beam are continuously irradiated while paying attention to the detection signal of the Si element mixed into a multi-film of the sample surface whereby the depth concentration distribution of the mixed Si was measured. The obtained results are shown in FIG. 16. When the multiply-charged ion is utilized as previously described, the depth analysis of the element can be analyzed with the resolution at the atom layer level. Also in this embodiment, the situation in which the Si concentration changes in a step function manner every layer boundary of the multi-film formed on the sample surface can be measured. Further, in the case that an ion generated from the sample by irradiating the multiply-charged ion is analyzed, when an element of objective material changes, a neutralization probability of the ion on the sample surface changes whereby the detection sensitivity sometimes changes due to the difference of the element of objective material. On the other hand, however, the emission probability of the neutral particle is often nearly constant, and the analysis with good quantitative accuracy can be made. Also in the present embodiment, an analyzed value nearly as designed can be obtained. Further, a signal of an ion emitted from the sample and a signal of a neutral particle can be added to further improve the sensitivity.

While in the present embodiment, a mass analyzer was used for the analysis of a secondary particle emitted from the sample surface, it is to be noted that in the case that a laser beam having a wavelength capable of ionizing only the element to be analyzed is irradiated, the mass analyzer is not always used but a specific element can be analyzed.

As will be apparent from the foregoing, according to the present invention, the kind of atoms present in the top surface layer of the solid and the bonding state thereof can be determined immediately from the measured results, thus greatly contributing to an improvement in analyzing accuracy of various materials used in key industries such as electronics.

It is further understood by those skilled in the art that the foregoing description is a preferred embodiment of the disclosed device and that various changes and modifications may be made in the invention without departing from the spirit and scope thereof.

What is claimed is:

1. A surface analyzing method comprising:
   an ion generation step for generating multiply-charged ions of specific ion species and specific charge state;
   a deceleration step for decelerating the generated multiply-charged ions to a lower kinetic energy than an energy of threshold of sputtering of an objective material;
   an irradiation step for irradiating the decelerated multiply-charged ions on the surface of a sample; and
   an analysis step for analyzing particles or light emitted from the surface of said sample by the irradiation of said multiply-charged ions.

2. A surface analyzing method according to claim 1, wherein said ion generation step comprises an ion generation stage for generating ions including multiply-charged ions of said specific ion species and specific charge, and a separation step for separating said multiply-charged ions of said specific ion species and specific charge out of the generated ions.

3. A surface analyzing method according to claim 1, wherein said deceleration step is a step for decelerating said generated multiply-charged ions to a kinetic energy of no greater than 20 eV or less.

4. A surface analyzing method according to claim 1, wherein said deceleration step is a step for decelerating said generated multiply-charged ions to a kinetic energy of no greater than 1 KeV.

5. A surface analyzing method according to claim 1, wherein said analysis step is a step for analyzing a mass of particles emitted from said sample surface by the irradiation of said multiply-charged ions and a kinetic energy.

6. A surface analyzing method according to claim 1, wherein said analysis step is a step for analyzing a photon energy of light emitted from said sample surface by the irradiation of said multiply-charged ions.

7. A surface analyzing method according to claim 1, wherein said analysis step is a step for analyzing an Auger electron emitted from said sample surface by the irradiation of said multiply-charged ions.

8. A surface analyzing method according to claim 1, wherein said analysis step is a step for analyzing ions emitted from said sample surface by the irradiation of said multiply-charged ions.

9. A surface analyzing method according to claim 1, wherein said analysis step is a step for analyzing neutral particles emitted from said sample surface by the irradiation of said multiply-charged ions.

10. A surface analyzing method according to claim 1, wherein said analysis step is a step for analyzing ions of said neutral particles emitted obtained by irradiating a laser beam on the neutral particles emitted from said sample surface by the irradiation of said multiply-charged ions.

11. A surface analyzing method according to any of claim 1 to 4, wherein said analysis step is a step for analyzing elements sequentially emitted from said sample surface by sequentially etching said Sample surface by the irradiation of said multiply-charged ions to thereby measure a distribution depthwise from said sample surface of said emitted elements.

12. A surface analyzing method according to any of claim 1 to 4, wherein said irradiation step is a step for irradiating said multiply-charged ions on the surface of said sample while cooling said sample.

13. A surface analyzing method comprising:
an ion generation step for generating a plurality of multiply-charged ion which are the same in ion species and different in charge state from each other;
a deceleration step for decelerating the generated multiply-charged ions to a lower kinetic energy than an energy of threshold of sputtering of an objective material;
an irradiation step for sequentially irradiating the generated plurality of multiply-charged ions on the sample while changing the charge state thereof;
a step of Auger electron measurement for detecting Auger electrons sequentially emitted from the surface of said sample corresponding to the sequential irradiation of said plural multiply-charged ions and measuring a value of kinetic energy thereof; and
an analysis step for analyzing a composition of elements of materials present on said sample surface and a bonding state of said elements on the basis of the measured results in said step of Auger electron measurement.

14. A surface analyzing method according to claim 13, wherein said step of analysis comprises steps of:
obtaining a relation between a charge state of said multiply-charged ions irradiated on said sample surface and a detected value of said Auger electrons emitted from said sample surface,
calculating the charge state of the multiply-charged ions which have been irradiated on said sample when said Auger electron is first detected from said relation, and
analyzing the composition of elements of materials present on said sample surface and the bonding state of said elements from the calculated charge state of the multiply-charged ions and the kinetic energy of said Auger electron measured in said step of Auger electron measurement.

15. A surface analyzing method comprising:
an ion generation step for generating a plurality of multiply-charged ion which are the same in ion species and different in charge state from each other;
a deceleration step for decelerating the generated multiply-charged ions to a lower kinetic energy than an energy of threshold of sputtering of an objective material;
an ion irradiation step for irradiating the generated plurality of multiply-charged ions on the sample while sequentially changing the charge state thereof;
a step of secondary ion measurement for detecting secondary ion sequentially emitted from the surface of said sample corresponding to the sequential irradiation of said plurality of multiply-charged ions and measuring the number of masses or kinetic energy value; and
an analysis step for analyzing a composition of elements of materials present on said sample surface and a bonding state of said elements on the basis of the measured results in said step of secondary ion measurement.

16. A surface analyzing method according to claim 15, wherein said analysis step comprises steps of:
obtaining a relation between the charge state of said multiply-charged ions irradiated on said sample surface and the detected value of said secondary ions emitted from said sample surface on the basis of the measured results in said step of secondary ion measurement,
calculating the charge state of the multiply-charged ions which have been irradiated on said sample when the detected value of said secondary ions was rapidly increased from said relation, and
analyzing the composition of elements of materials present on said sample surface and the bonding state of said elements from the calculated charge state of the multiply-charged ions and the number of masses of said secondary ions measured in said step of secondary ion measurement or the kinetic energy value.

17. A surface analyzing apparatus comprising:
an ion generator for generating multiply-charged ions of specific ion species and specific charge state;
a decelerator for decelerating the generated multiply-charged ions to a lower kinetic energy than an energy of threshold of sputtering of an objective material;
an irradiator for irradiating the decelerated multiply-charged ions on the surface of a sample; and
an analysis means for analyzing particles or light emitted from the surface of said sample by the irradiation of said multiply-charged ions.

18. A surface analyzing apparatus according to claim 17, wherein said ion generator comprises an ion generation means for generating ions including multiply-charged ions of said specific ion species and specific charge, and a separator for separating said multiply-charged ions of said specific ion species and specific charge out of the generated ions.

19. A surface analyzing apparatus according to claim 17, wherein said decelerator is a means for decelerating said generated multiply-charged ions to a kinetic energy of no greater than 20 eV.

20. A surface analyzing apparatus according to claim 17, wherein said decelerator is a means for decelerating said generated multiply-charged ions to a kinetic energy of no greater than 1 KeV.

21. A surface analyzing apparatus according to claim 17, wherein said analysis means is a means for analyzing a mass of particles emitted from said sample surface by the irradiation of said multiply-charged ions and a kinetic energy.

22. A surface analyzing apparatus according to claim 17, wherein said analysis means is a means for analyzing a photon energy of light emitted from said sample surface by the irradiation of said multiply-charged ions.

23. The surface analyzing apparatus according to claim 17, wherein said means of analysis comprises a means for analyzing an Auger electron emitted from said sample surface by the irradiation of said multiply-charged ions.

24. A surface analyzing apparatus according to claim 17, wherein said analysis means is a means for analyzing ions emitted from said sample surface by the irradiation of said multiply-charged ions.

25. A surface analyzing apparatus according to claim 17, wherein said analysis means is a means for analyzing neutral particles emitted from said sample surface by the irradiation of said multiply-charged ions.

26. A surface analyzing apparatus according to claim 17, wherein said analysis means is a means for analyzing ions of said neutral particles emitted obtained by irradiating a laser beam on the neutral particles emitted from said sample surface by the irradiation of said multiply-charged ions.

27. The surface analyzing apparatus according to any of claim 17 to 20, wherein said analysis means is a means for analyzing elements sequentially emitted from said sample surface by sequentially etching said sample surface by the irradiation of said multiply-charged ions to thereby measure a distribution depthwise from said sample surface of said emitted elements.

28. A surface analyzing apparatus according to any of claim 17 to 20, wherein said irradiator is a means for irradiating said multiply-charged ions on the surface of said sample while cooling said sample.

29. A surface analyzing apparatus according to claim 28, wherein said analysis means is a means for obtaining a relation between a charge state of said multiply-charged ions irradiated on said sample surface and a detected value of said Auger electrons emitted from said sample surface, calculating the charge state of the multiply-charged ions which have been irradiated on said sample when said Auger electron is first detected from said relation, and analyzing the composition of elements of materials present on said sample surface and the bonding state of said elements from the calculated charge state of the multiply-charged ions and the kinetic energy of said Auger electron measured in said step of Auger electron measurement.

30. A surface analyzing method comprising:

an ion generator for generating a plurality of multiply-charged ion which are the same in ion species and different in charge state from each other;

an ion decelerator for decelerating the generated multiply-charged ions to a lower kinetic energy than an energy of threshold of sputtering of an objective material;

an ion irradiation step for sequentially irradiating the generated plurality of multiply-charged ions on the sample while changing the charge state thereof;

a means of Auger electron measurement for detecting Auger electrons sequentially emitted from the surface of said sample corresponding to the sequential irradiation of said plurality of multiply-charged ions and measuring a value of kinetic energy thereof; and an analysis means for analyzing a composition of elements of materials present on said sample surface and a bonding state of said elements on the basis of the measured results in said step of Auger electron measurement.

31. A surface analyzing method comprising:

an ion generator for generating a plurality of multiply-charged ions which are the same in ion species and different in charge state from each other;

an ion decelerator for decelerating the generated multiply-charged ions to a lower kinetic energy than an energy of threshold of sputtering of an objective material;

an ion irradiator for irradiating the generated plural of multiply-charged ions on the sample while sequentially changing the charge state thereof;

a means of secondary ion measurement for detecting secondary ions sequentially emitted from the surface of said sample corresponding to the sequential irradiation of said plurality of multiply-charged ions and measuring the number of masses or kinetic energy value; and an analysis means for analyzing a composition of elements of materials present on said sample surface and a bonding state of said elements on the basis of the measured results in said step of secondary ion measurement.

32. A surface analyzing apparatus according to claim 31, wherein said analysis means is a means for obtaining a relation between the charge state of said multiply-charged ions irradiated on said sample surface and the detected value of said secondary ions emitted from said sample surface on the basis of the measured results in said secondary ion measurement, calculating the charge state of the multiply-charged ions which have been irradiated on said sample when the detected value of said secondary ions was rapidly increased from said relation, and analyzing the composition of elements of materials present on said sample surface and the bonding state of said elements from the calculated charge state of the multiply-charged ions and the number of masses of said secondary ions measured in said secondary ion measurement or the kinetic energy value.

* * * * *